(12) United States Patent
Austera et al.

(10) Patent No.: US 9,267,911 B2
(45) Date of Patent: Feb. 23, 2016

(54) ENCODED BIOSENSORS AND METHODS OF MANUFACTURE AND USE THEREOF

(71) Applicant: Roche Diabetes Care, Inc., Indianspolis, IN (US)

(72) Inventors: John T. Austera, Indianapolis, IN (US); Terry A. Beaty, Indianapolis, IN (US); Abner D. Joseph, Carmel, IN (US); Nathan E. Manlove, Noblesville, IN (US); Steven K. Moore, Carmel, IN (US); James L. Pauley, Jr., Fishers, IN (US); Randall K. Riggles, Indianapolis, IN (US)

(73) Assignee: Roche Diabetes Care, Inc., Indianpolis, IN (US)

( * ) Notice: Subject to any disclaimer, the term of this patent is extended or adjusted under 35 U.S.C. 154(b) by 0 days.

(21) Appl. No.: 14/542,755

(22) Filed: Nov. 17, 2014

(65) Prior Publication Data

US 2015/0076010 A1     Mar. 19, 2015

Related U.S. Application Data

(63) Continuation of application No. 13/194,031, filed on Jul. 29, 2011, now Pat. No. 8,888,973.

(51) Int. Cl.
*G01N 27/327*     (2006.01)
*G01N 33/487*     (2006.01)

(52) U.S. Cl.
CPC ...... *G01N 27/3272* (2013.01); *G01N 33/48771* (2013.01)

(58) Field of Classification Search
CPC ........ G01N 27/327–27/3273; G01N 33/48771
See application file for complete search history.

(56) References Cited

U.S. PATENT DOCUMENTS

| 6,689,320 B1 | 2/2004 | Markart |
| 7,418,285 B2 | 8/2008 | Ghesquiere et al. |

(Continued)

FOREIGN PATENT DOCUMENTS

| EP | 1431758 A1 | 6/2004 |
| EP | 2051072 A2 | 4/2009 |

(Continued)

OTHER PUBLICATIONS

European Patent Office, International Search Report and Written Opinion of the International Searching Authority, PCT Application No. PCT/EP2012/003131, Oct. 25, 2012, Rijswijk, The Netherlands.

(Continued)

*Primary Examiner* — J. Christopher Ball
(74) *Attorney, Agent, or Firm* — Quarles & Brady, LLP

(57) ABSTRACT

An analyte test sensor strip is disclosed having information coded thereon as well as a method of forming the same and conducting an analyte test using the analyte test sensor strip. Information relating to an attribute of the strip or batch/lot of strips may be coded based on resistance values pertaining to electrical aspects of the strip, such as a primary resistive element and a secondary resistive element, the secondary resistive element having one of a plurality of states defined by a location of a closed tap to form a unique resistive path for the secondary resistive element that includes a portion of the primary resistive element depending on the location of the closed tap. The states may be formed on the strip by a secondary processing step in the manufacture of the strip in which a plurality of taps are severed leaving only one tap in a closed state.

8 Claims, 17 Drawing Sheets

(56) References Cited

U.S. PATENT DOCUMENTS

| | | |
|---|---|---|
| 7,474,391 B2 | 1/2009 | Baskeyfield et al. |
| 7,491,303 B2 | 2/2009 | Sakata et al. |
| 7,556,723 B2 | 7/2009 | Funke et al. |
| 7,569,126 B2 | 8/2009 | Celentano et al. |
| 7,593,097 B2 | 9/2009 | Robinson et al. |
| 7,601,299 B2 | 10/2009 | Beaty et al. |
| 7,625,473 B2 | 12/2009 | Hsu |
| 7,645,373 B2 | 1/2010 | Groll et al. |
| 7,645,421 B2 | 1/2010 | Groll |
| 7,713,392 B2 | 5/2010 | Harding et al. |
| 7,718,439 B2 | 5/2010 | Groll |
| 7,809,512 B2 | 10/2010 | Perry |
| 7,829,023 B2 | 11/2010 | Burke et al. |
| 7,846,321 B2 | 12/2010 | Diamond et al. |
| 7,892,849 B2 | 2/2011 | Burke et al. |
| 2005/0279647 A1 | 12/2005 | Beaty |
| 2007/0273903 A1 | 11/2007 | Baskeyfield et al. |
| 2008/0267823 A1 | 10/2008 | Wang et al. |
| 2008/0291451 A1 | 11/2008 | Cheng et al. |
| 2009/0030617 A1 | 1/2009 | Schell et al. |
| 2009/0159197 A1 | 6/2009 | Edelbrock |
| 2009/0288964 A1 | 11/2009 | Jung et al. |
| 2010/0084466 A1 | 4/2010 | Charlton et al. |

FOREIGN PATENT DOCUMENTS

| | | |
|---|---|---|
| KR | 20070026606 A1 | 3/2007 |
| WO | 2006072089 A1 | 7/2006 |

OTHER PUBLICATIONS

Korean Intellectual Property Office, Notice of Grounds for Rejection, Patent Application No. 2014-7002580, Sep. 10, 2015 [English Language Translation Only].

US 7,871,567, 01/2011, Beaty et al. (withdrawn)

ENCODED BIOSENSORS AND METHODS OF MANUFACTURE AND USE THEREOF

CROSS-REFERENCE TO RELATED APPLICATIONS

This patent application is a continuation of U.S. patent application Ser. No. 13/194,031(filed 29 Jul. 2011), now U.S. Pat. No. 8,888,973 (issued 18 Nov. 2014), which is incorporated herein by reference as if set forth in its entirety.

FIELD OF THE INVENTION

The present invention relates generally to an analyte test sensor for use in measuring concentrations of an analyte in a biological fluid and, more particularly, to an analyte test strip having coding information formed thereon.

BACKGROUND

Biosensors provide an analysis of a biological fluid, such as whole blood, urine, or saliva. Measuring the concentration of substances in biological fluids is an important tool for the diagnosis and treatment of many medical conditions. For example, the measurement of glucose in body fluids, such as blood, is crucial to the effective treatment of diabetes. The sample of biological fluid may be directly collected or may be a derivative of a biological fluid. Typically, biosensors have a nondisposable measurement device or test meter that is used to analyze the sample of biological fluid that is placed on the test strip.

Many biosensor systems provide calibration information to the measurement device prior to the analysis. The measurement device typically uses this information to adjust the analysis of the biological fluid in response to one or more parameters. The accuracy and precision of the analysis is improved by using the calibration information. If the calibration information is not used, the measurement device may not complete the analysis or may make a wrong analysis of the concentration of the analyte in the biological fluid.

It is common practice in such test meter/test strip systems to ensure proper identification of the test strip in order to ensure proper test results. For example, a single test meter may be able to analyze several different types of test strips, wherein each type of test strip is designed to test for the presence or concentration of a different analyte in the biological fluid. In order to properly conduct the test, the test meter must know which type of test is to be performed for the test strip currently in use.

Also, lot-to-lot variations in the test strips normally require calibration information to be loaded into the test meter in order to ensure accurate test results. A common practice for downloading such calibration information into the test meter is the use of an electronic read-only memory key (ROM key) that is inserted into a corresponding slot or socket of the test meter. Because this calibration data may only be accurate for a particular production lot of test strips, the user is usually asked to confirm that the lot number of the test strip currently in use matches the lot number for which the ROM key was programmed.

Many other instances in which it is desirable to have information relating to the test strip are known to those having skill in the art. Prior art attempts to code information onto the test strip for reading by the test meter have suffered from many problems, including a severely limited amount of information that can be coded and the use of relatively large amounts of test strip surface area for the information coding function.

Thus, a system and method are needed that will allow information to be coded onto a biosensor for reading of the information by the test meter.

SUMMARY

One aspect of the present invention discloses an analyte test sensor strip that is used to measure the presence or concentration of an analyte in a fluid sample. The test sensor strip includes a non-conductive substrate. In addition, the test sensor strip includes an outer or primary resistive element formed on the non-conductive substrate having a first end and a second end. The primary resistive element has a predetermined configuration, which is a serpentine configuration in one form having a plurality of proximal ends and a plurality of distal ends. In addition, an inner or secondary resistive element is also formed on the non-conductive substrate having a tap connected to the primary resistive element at a predetermined connection point on the predetermined configuration thereby defining a unique resistive path through at least a portion of the predetermined configuration.

The unique resistive path through the predetermined configuration has associated therewith a resistance falling within a respective one of a plurality of ranges of resistances. The resistance is determined based on or as a function of a location of the predetermined connection point on the predetermined configuration. The unique resistive path is associated with an attribute of the analyte test sensor strip. An attribute of the strip should be broadly understood to refer to any information relating to the strip, such as strip type, calibration information, manufacturing information, country information, etc. Essentially any information pertaining to the strip which may be desirable to convey to a meter with which the strip is used.

In order to provide an opportunity to define the unique resistive path from among more than one possible unique resistive paths each having an associated resistance correlating to a different attribute, the secondary resistive element includes a plurality of taps. The respective tap that is connected with the predetermined configuration at the predetermined connection point is formed or maintained in a closed state and all other taps of the plurality of taps are opened or formed in an open state.

The first end of the primary resistive element is connected with a first contact pad and the second end is connected with a second contact pad. The secondary resistive element has a third end connected with a third contact pad. The unique resistive path runs from the third contact pad through the secondary resistive element and then into the primary resistive element at the predetermined connection point and then through at least a portion of the primary resistive element to one of the first and second contact pads.

Another aspect of the present invention discloses an analyte test sensor strip that is used to measure the concentration of an analyte in a fluid sample. The test sensor strip includes a non-conductive substrate. A primary resistive element is formed on the non-conductive substrate having a predetermined configuration with a first end connected with a first contact pad and a second end connected with a second contact pad. A secondary resistive element is also formed on the non-conductive substrate having a plurality of taps. One tap of the plurality of taps is connected with the primary resistive element at a predetermined location thereby being formed and/or maintained in a closed state and defining a unique resistive path through at least a portion of the primary resistive network. The remaining taps of the plurality of taps are opened or formed in an open state thereby being disconnected from the primary resistive network. A portion of the secondary resistive element is connected with a secondary resistive element contact pad.

In one form, the taps that are in the open state are ablated with a laser. The unique resistive path is associated with an attribute of the analyte test sensor strip. In one form, the attribute is associated with one or more algorithm variables, such as slope and/or intercept for a linear correlation algorithm, associated with the test sensor strip. In yet another form, the analyte test sensor strip includes an optical code formed on the non-conductive substrate. The optical code can contain information related to the test sensor strip such as a product expiration date, product identification (countries or regions), intercepts of blood and control solutions, strip lot identification, and other features. In addition, the test sensor strip can also include a first resistance loop formed on the non-conductive substrate comprising a first measurement sense electrode in a spaced apart relationship from a first measurement electrode. In one form, the first measurement electrode is connected with the second end of the primary resistive element.

Another aspect of the present invention discloses a method of forming a biosensor test strip that is utilized to measure the concentration of an analyte. In this aspect, a primary resistive element is formed on a non-conductive substrate having a predetermined configuration including a first end and a second end. Further, a secondary resistive element is formed on the non-conductive substrate having at least one tap connected to a predetermined connection location on the primary resistive element thereby defining a unique resistive path through at least a portion of the primary resistive element having associated therewith a resistance falling within a respective one of a plurality of ranges of resistances.

The secondary resistive element is formed to include a plurality of taps. All of the plurality of taps but the tap connected to the predetermined location on the primary resistive element are ablated thereby disconnecting the ablated taps from the primary resistive element. The primary resistive element includes a plurality of predetermined connection locations. A connection location to be connected with the tap is selected as a function of an attribute associated with the biosensor test strip. The unique resistive path through the secondary and primary resistive elements is associated with an attribute of the biosensor test strip. Further, each range of resistances contained in the plurality of ranges of resistances is associated with a unique attribute of the biosensor test strip.

Yet another aspect of the present invention discloses an analyte test sensor strip that is used to measure the concentration of an analyte. The test sensor strip includes a non-conductive substrate. In addition, the test sensor strip includes means for conducting quantitative or qualitative analysis of the analyte in a sample of fluid. An information circuit is provided on the non-conductive substrate. The information circuit includes a conductive primary path between a first end and a second end having a predetermined configuration between the first and second ends. The conductive primary path has a resistance falling within a first predetermined range. The information circuit also includes a conductive secondary path between the first end of the conductive primary path and a third end. The conductive secondary path is substantially defined by a plurality of open taps and a closed tap. The closed tap selectively connects the third end with the conductive primary path at a predetermined location thereby defining a unique resistive path between the first end and the third end through at least a portion of the conductive primary path. The unique resistive path has a second resistance falling within a second predetermined range.

In one form, a ratio of the first resistance and the second resistance selectively correlates to an attribute of the analyte test sensor strip. The first end is connected with a first contact pad, the second end is connected with a second contact pad, and the third end is connected with a third contact pad. In one form, the predetermined configuration comprises a serpentine configuration having a plurality of proximal ends and a plurality of distal ends. The closed tap is connected to a respective proximal end of the serpentine configuration. The tap that comprises the closed tap is selected as a function of an attribute of the analyte test sensor strip.

Another aspect discloses a method for measuring a concentration of an analyte in a sample of fluid. The method comprises the steps of providing a test meter; providing a test strip, said test strip comprising: a non-conductive substrate; a working electrode on the non-conductive substrate connectable to the test meter; a counter electrode on the non-conductive substrate connectable to the test meter; a reagent part bridging between the working electrode and the counter electrode; a primary resistive element on the non-conductive substrate having a first end connectable to the test meter and a second end connectable to the test meter, wherein the primary resistive element has a predetermined configuration; and a secondary resistive element on the non-conductive substrate having a third end connectable to the test meter, wherein the secondary resistive element has a tap connected to the primary resistive element at a predetermined connection point on the predetermined configuration thereby defining a unique resistive path through at least a portion of the predetermined configuration having a resistance value; receiving the test strip into the test meter; operatively connecting the working electrode, the counter electrode, the primary resistive element, and the secondary resistive element with the test meter; and determining an attribute associated with the test strip as a function of a measurement associated with at least the resistance value associated with the unique resistive path.

In one form, the primary resistive element has a primary element resistance value and the attribute is determined as a function of a resistance ratio determined by comparing the resistance value of the unique resistive path with the primary element resistance value. The test meter is adjusted to output a concentration measurement output associated with the analyte as a function of the attribute. In one form, an end of the primary resistive element is connected with the counter electrode.

BRIEF DESCRIPTION OF THE DRAWINGS

The invention is further elucidated in the following on the basis of an exemplary embodiment shown in the drawings.

FIGS. 3b and 3c illustrate alternative embodiments of a portion of the test strip illustrated in FIG. 3a.

FIG. 4 illustrates a portion of the test strip illustrated in FIG. 3a.

DETAILED DESCRIPTION

Figure 1:
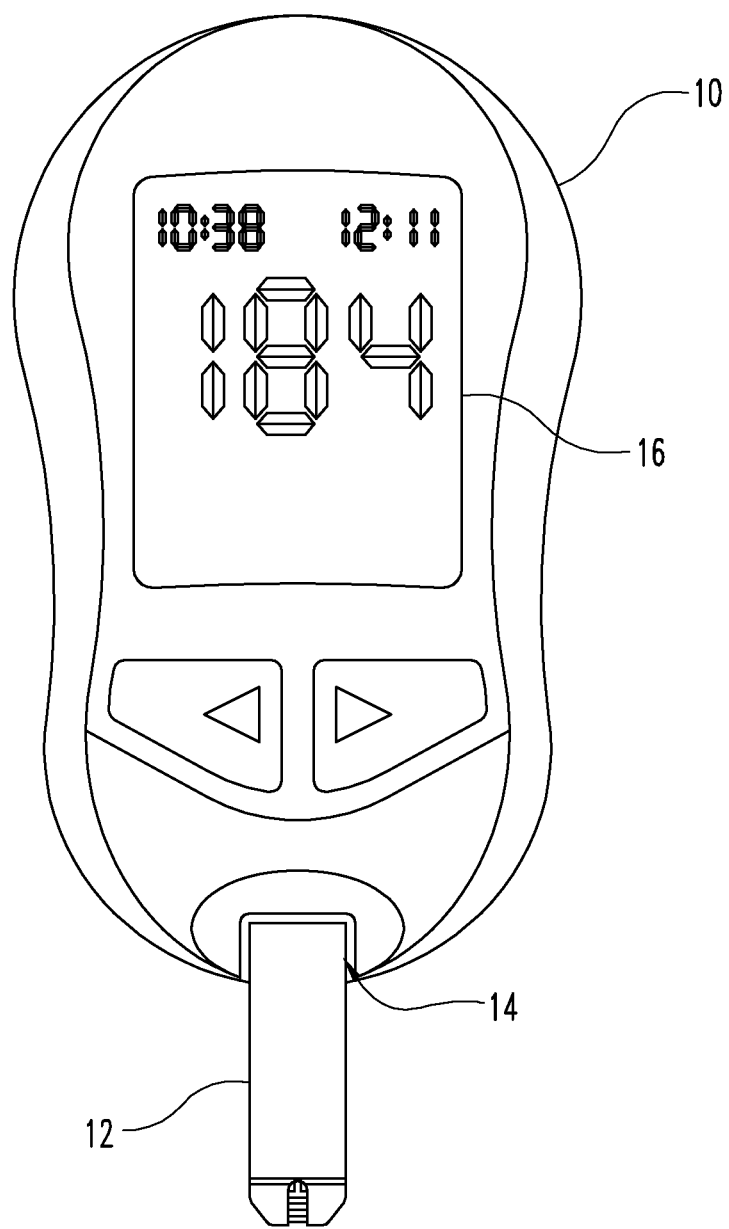
FIG. 1 illustrates a test strip inserted into a test meter.

For the purposes of promoting an understanding of the principles of the invention, reference will now be made to the embodiment illustrated in the drawings, and specific language will be used to describe that embodiment. It will nevertheless be understood that no limitation of the scope of the invention is intended. Alterations and modifications in the illustrated device, and further applications of the principles of the invention as illustrated therein, as would normally occur to one skilled in the art to which the invention relates are contemplated, are desired to be protected. In particular, although the invention is discussed in terms of a blood glucose meter, it is contemplated that the invention can be used with devices for measuring other analytes and other sample types. Such alternative embodiments require certain adaptations to the embodiments discussed herein that would be obvious to those skilled in the art.

Referring to FIG. 1, a concentration measuring device or test meter 10 is disclosed with an analyte test sensor strip 12 mounted thereto that is used to measure the presence or concentration of an analyte in a biological fluid, such as whole blood, urine, or saliva. In this form, the test strip 12 is removably inserted into a connection terminal 14 of the test meter 10. Upon insertion of the test strip 12, the test meter 10 is configured to automatically turn on and begin the measuring process, as set forth in greater detail below. The test meter 10 includes an electronic display 16 that is used to display various types of information to the user including the test results.

Figure 2:
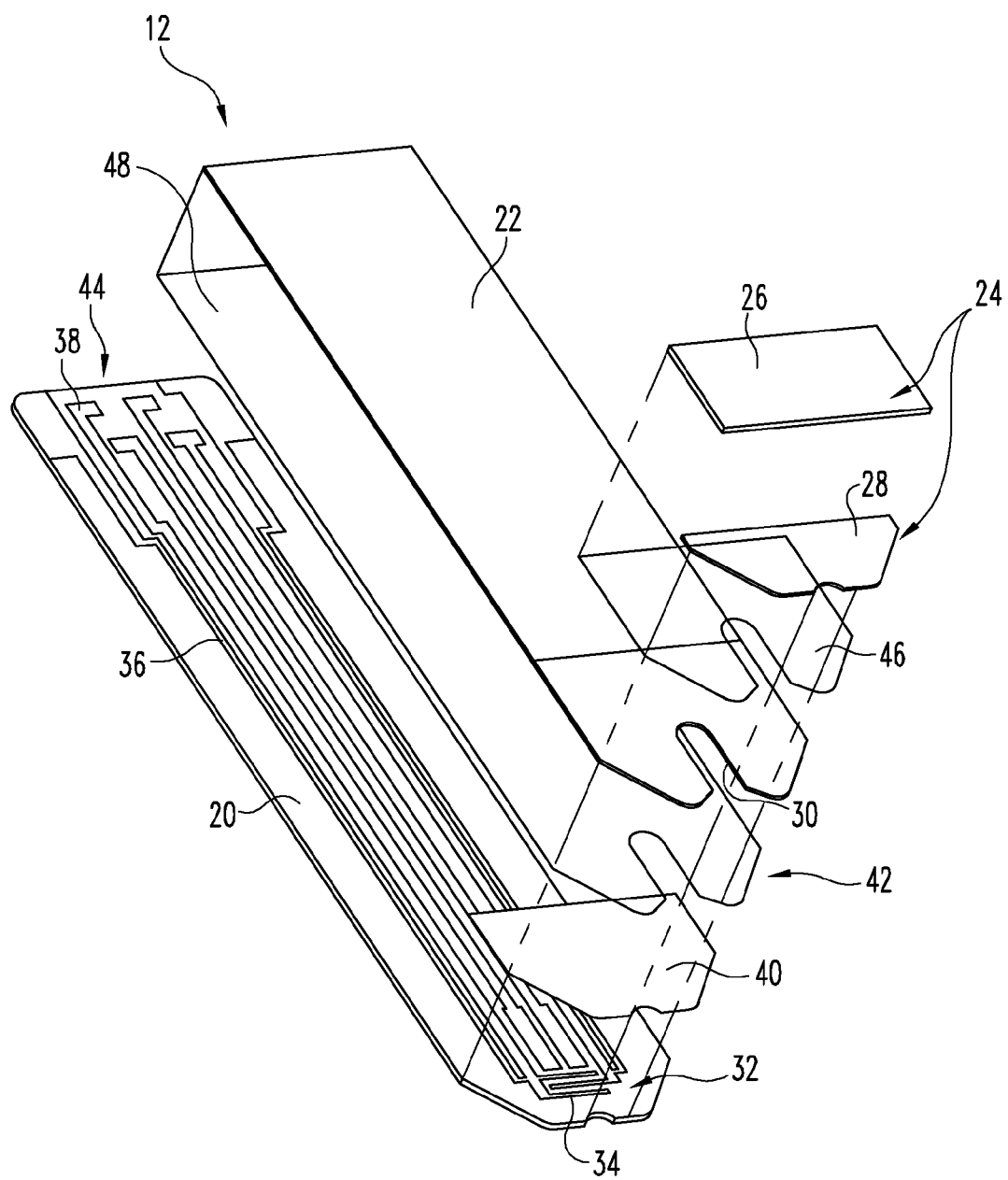
FIG. 2 is an exploded view of a representative test strip.

Referring to FIG. 2, a general test strip 12 is illustrated for background purposes and includes several components. The test strip 12 comprises a small body defining a chamber in which the sample fluid is received for testing. This sample-receiving chamber is filled with the sample fluid by suitable means, preferably by capillary action, but also optionally assisted by pressure or vacuum. The sample-receiving chamber includes electrodes and chemistry suitable for producing an electrochemical signal indicative of the analyte in the sample fluid.

In this illustrated form, the test strip 12 includes a base substrate 20, a spacing layer 22 and a covering layer 24 comprising body cover 26 and chamber cover 28. The spacing layer 22 includes a void portion 30 to provide a sample receiving chamber extending between the base substrate 20 and the covering layer 24. The base substrate 20 carries an electrode system 32 including a plurality of electrodes 34 and electrode traces 36 terminating in contact pads 38. The electrodes 34 are defined as those portions of the electrode traces 36 that are positioned within the sample-receiving chamber. A suitable reagent system 40 overlies at least a portion of the electrodes 34 within the sample-receiving chamber.

The body cover 26 and the chamber cover 28 overlying the spacing layer 22 define a slot therebetween, the slot defining a vent opening communicating with the sample-receiving chamber to allow air to escape the chamber as a sample fluid enters the chamber from the edge opening or fluid receiving opening. The test strip 12 therefore includes a dosing end 42 and a meter insertion end 44. The shape of the dosing end 42 is typically distinguishable from the meter insertion end 44 so as to aid the user. The body cover 26 and chamber cover 28 are preferably secured to the spacing layer 22 by an adhesive layer 46. Further, a second adhesive layer 48 secures the spacing layer 22 to the base substrate 20. A more detailed discussion of the test strip 12 illustrated in FIG. 2 can be found in commonly owned U.S. Pat. No. 7,829,023, which is hereby incorporated by reference in its entirety.

Figure 3A:
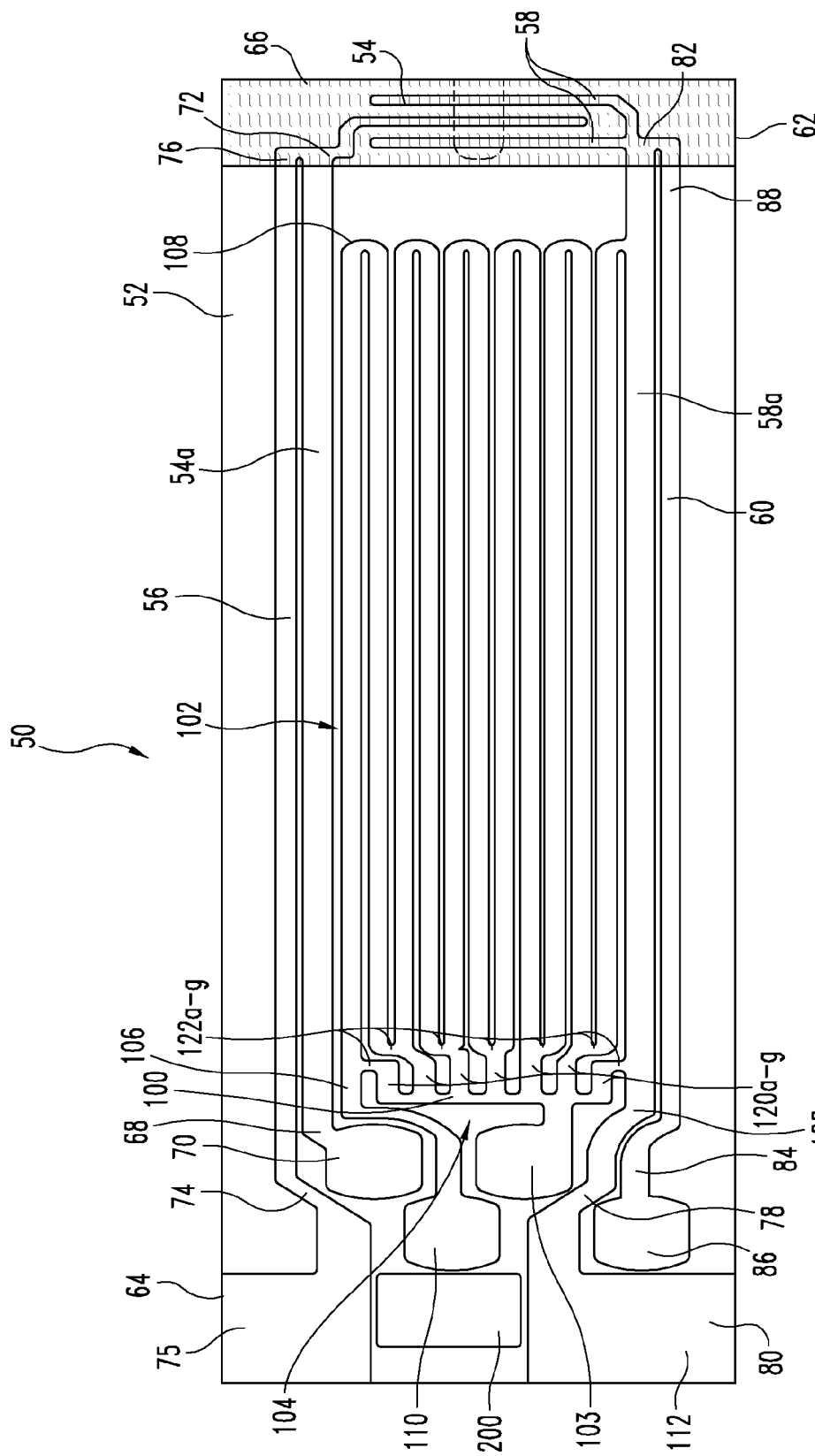
FIG. 3a illustrates a test strip for use in measuring the concentration of an analyte of interest in a biological fluid.

Referring to FIG. 3a, a more detailed image of one preferred form of a test strip 50 that is configured for use with the test meter 10 is illustrated having spacer, covering and adhesive layers removed to reveal the electrode system 32 of the test strip 50. The test strip 50 includes a non-conductive base substrate 52 having formed thereon a plurality of electrodes, traces and contact pads, as will be discussed in greater detail below. Such formation may be achieved by using any of a number of known techniques, such as screen printing, lithography, laser scribing or laser ablation. For purposes of illustration, formation using a broad field laser ablation technique is generally described herein.

Prior to formation of the electrodes, traces and contact pads, the non-conductive substrate is coated on its top surface with a conductive layer (by sputtering or vapor deposition, for example). The electrodes, traces and contact pads are then patterned in the conductive layer formed on the non-conductive substrate by a laser ablation process using a mask defining the desired design for the electrical aspects of the test strip. A more detailed discussion of the laser ablation process is set forth in commonly owned U.S. Pat. No. 7,601,299, which is hereby incorporated by reference in its entirety.

The conductive layer may contain pure metals or alloys, or other materials, which are metallic conductors. The conductive material is generally absorptive at the wavelength of the laser used to form the electrodes, traces and contact pads on the non-conductive substrate 52. Non-limiting examples include aluminium, carbon, copper, chromium, gold, indium tin oxide, palladium, platinum, silver, tin oxide/gold, titanium, mixtures thereof, and alloys or metallic compounds of these elements. In some forms, the conductive material includes noble metals or alloys or their oxides.

The test strip 50 includes a working electrode 54, a working sense trace 56, a counter electrode 58, and a counter sense trace 60 formed on the non-conductive substrate 52. The test strip 50 includes a distal end or reaction zone 62 and a proximal end or contact zone 64 extending along a longitudinal axis. As set forth in greater detail below, the test strip 50 includes a working electrode trace 54a that is used to connect the working electrode 54 to a contact pad 70. Further, the test strip 50 includes a counter electrode trace 58a that is used to connect the counter electrode 58 to a contact pad 80. As illustrated, the proximal end 64 of the test strip 50 includes a plurality of contact pads that are configured to be conductively connected with the connection terminal 14 of the test meter 10. In one form, the test meter 10 is configured to determine the type of test strip 50 inserted into the test meter 10 based on the configuration, including, e.g., any interconnection, of the contact pads. The distal end 62 of the test strip 12 includes a reagent layer 66 that covers at least a portion of the working electrode 54 and counter electrode 58.

The reagent layer 66 of the test strip 50 may comprise reagents of a chemical or biochemical nature for reacting with a target analyte to produce a detectable signal that represents the presence and/or concentration of the target analyte in a sample. The term "reagent", as used herein, is a chemical, biological or biochemical reagent for reacting with the analyte and/or the target to produce a detectable signal that represents the presence or concentration of the analyte in the sample. Suitable reagents for use in the different detection systems and methods include a variety of active components selected to determine the presence and/or concentration of various analytes, such as glucose for example. The selection of appropriate reagents is well within the skill in the art. As is well known in the art, there are numerous chemistries available for use with each of various targets. The reagents are selected with respect to the target to be assessed. For example, the reagents can include one or more enzymes, co-enzymes, and co-factors that can be selected to determine the presence of glucose in blood.

The reagent chemistry may include a variety of adjuvants to enhance the reagent properties or characteristics. For example, the chemistry may include materials to facilitate the placement of the reagent composition onto the test strip 50 and to improve its adherence to the strip 50, or for increasing the rate of hydration of the reagent composition by the sample fluid. Additionally, the reagent layer can include components selected to enhance the physical properties of the resulting dried reagent layer 66, and the uptake of a liquid test sample for analysis. Examples of adjuvant materials to be used with the reagent composition include thickeners, viscosity modulators, film formers, stabilizers, buffers, detergents, gelling agents, fillers, film openers, coloring agents, and agents endowing thixotropy.

As further illustrated in FIG. 3a, a proximal end 68 of the working electrode trace 54a is connected with a working electrode measurement contact pad 70. A distal end 72 of the working electrode trace 54a is connected with the working electrode 54. A proximal end 74 of the working sense trace 56 is connected with a working sense measurement contact pad 75. As further illustrated, a distal end 76 of the working sense trace 56 is connected with the distal end 72 of the working electrode trace 54a thereby defining a working resistance loop.

In one form, the working resistance loop has a resistance value within a predetermined range of resistance values, which range corresponds to an attribute of the test strip 12. Forming the working resistance loop to have a resistance value that falls within one or another predetermined range of resistance values is within the ordinary skill in the art of forming thin conductive layers. Nevertheless, for purposes of illustration, it is known that conductive materials, such as thin layers of metals such as gold and palladium, have a characteristic sheet resistance dependent upon the thickness of the conductive layer. Sheet resistance is essentially a multiplier for calculating a predicted resistance through a path of a particular configuration (e.g. length and width) for a particular material of a particular thickness. Thus, sheet resistance and/or the configurational aspects of the conductive trace can be altered in order to achieve a desired resistance through a particular path, such as the working resistance loop.

Thus, for example, a gold layer having a thickness of 50 ηm has a sheet resistance of 1.6 ohms/square. A "square" is a unitless measure of the aspect ratio of the conductive path, broken down into the number of square sheets (based on the width) that can be actually or theoretically determined in the conductive path. In one sense, the effective surface area of the conductive path is approximated as a number of squares. The number of squares that can be determined in the conductive path is multiplied by the sheet resistance to give a calculation for a predicted resistance through that conductive path.

In the context of the present invention, illustrative and exemplary embodiments will typically be described in the context of 50 ηm thick layers of gold, thus a sheet resistance of 1.6 ohms/square. Thus, in order to manipulate the resistance along any conductive paths being described in the various contexts of this disclosure (as will be clear to persons of ordinary skill in the art), one may alter the length or width of the conductive path (thus change the number of "squares") or one may alter the thickness or material of the conductive layer (thus changing the sheet resistance) in order to increase or decrease a predicted resistance value for that particular conductive path to fall within a desired range of resistance values, wherein the range of such values is indicative of an attribute of the test strip. Determining the number of squares for a particular conductive path in a variety of patterns and configurations other than generally straight line paths is within the ordinary skill in the art and requires no further explanation here.

As will be further described, actual measured resistance values through variously identified conductive paths included in the embodiments of the present invention are used in various manners for purposes of indicating one or more attributes of a test strip. In this regard, it will be understood that the measured resistance values, or predetermined ranges of resistance values in which a measured resistance value lies, or ratios of the measured resistance values between different conductive paths, may correspond to a particular attribute. Which of these manners is employed for corresponding the resistance value of a conductive path to an attribute is within the discretion of the person of ordinary skill in the art.

Generally, the measured resistance value itself is useful in the event the actual, measured resistance value closely corresponds to the predicted resistance value (calculated as described above). If manufacturing tolerances are such that the measured value does not correspond well to the predicted value, then it may be advisable to predetermine a range of resistance values within which a conductive path having a certain predicted resistance value will almost certainly have a measured resistance value. In that case, the system measures the actual resistance value of a conductive path, identifies the predetermined the range within which the resistance value lies, and corresponds that identified predetermined range with the attribute of the test strip. Finally, if manufacturing tolerances are simply not conducive to accurately predicting the actual measured resistance value for a conductive path, or simply as desired, it may be useful to ratio one measured resistance value against another measured resistance value through a different conductive path, in order to determine an essentially normalized value. The normalized value may be used similarly as a measured resistance value or compared against one or more predetermined ranges of values in order to identify a corresponding attribute of the test strip. It is generally in this context of measured, predicted, and normalized resistance values that the present invention will be further described and understood.

For illustrative purposes only, in one form the working resistance loop has a resistance value of approximately 380.8 Ohms (In this illustrative form, it is assumed that 50 ηm thick gold is used to form the traces and contact pads and that the surface area associated with the traces and contact pads of the working resistance loop equates to approximately 238 squares. As such, the working resistance loop has a resistance value of approximately 380.8 Ohms.) In one embodiment, this resistance value is within a predetermined range, e.g. 250-450 Ohms, and corresponds to an attribute such as the strip type, i.e. a reagent deposited on the strip that is configured for determination of glucose concentration. By way of example, a different predetermined range, e.g. 550-750 Ohms, for the resistance value of the working resistance loop may correspond to a different strip type, such as for determination of ketone concentration. As with all forms, and as described above, the resistance value of the working resistance loop as well as all resistance values disclosed herein can be adjusted by various methods, such as, for example, by adjusting the length, width, and thickness of the working sense trace 56 as well as the material from which the working sense trace 56 is manufactured. See, for example, U.S. Pat. No. 7,601,299, the disclosure of which is hereby incorporated by reference herein.

A proximal end 78 of the counter electrode trace 58a is connected with a counter electrode measurement contact pad 80. A distal end 82 of the counter electrode trace 58a is connected with the counter electrode 58. In addition, a proximal end 84 of the counter sense trace 60 is connected with a counter sense measurement contact pad 86. A distal end 88 of the counter sense trace 60 is connected with the distal end 82 of the counter electrode trace 58a thereby defining a counter resistance loop. In one form, the counter resistance loop has a resistance value within a predetermined range of resistance values, which range corresponds to an attribute of the test strip 50. For illustrative purposes only, in one form the counter resistance loop has a resistance value of approximately 384 Ohms, based on a 50 ηm thick layer of gold and a surface area configuration of approximately 240 squares. In one embodiment, this resistance value is within a predetermined range, e.g. 250-450 Ohms, which range corresponds to an attribute of the test strip. In other embodiments, the resistance value of the working resistance loop is ratioed with the resistance value of the counter resistance loop wherein the ratio value corresponds to an attribute of the strip, such as strip type or geographic market of distribution.

As will be generally understood, designating an electrode as a "working" or "counter" electrode is merely an indication of a particular predetermined functionality or intended use for an electrode during an electrochemical measurement method as either an anode or cathode in the presence of a particular electrical field or applied potential. Those of ordinary skill in the art will similarly understand reference to such electrodes generically as first and second measurement electrodes (and corresponding traces, sense traces, contact pads, etc.), inasmuch as such electrodes participate in the measurement of a particular analyte or target, in contrast to, for example, electrodes that may be specifically designated solely for use as dose detecting and/or sample sufficiency electrodes according to known techniques; see, for example, U.S. Pat. No. 7,905,997, the disclosure of which is hereby incorporated herein by reference. In view of these understandings, the designations "working" and "counter" are used solely for contextual illustration and description, and are not intended to limit the scope of the present invention, whether or not recited in the claims, to a particular measurement electrode functionality.

Generally speaking, in order to commence an assay, the test sensor 50 is inserted into the connection terminal 14 of the test meter 10 such that all of the contact pads of the test sensor 50 are connected to contact pins within the connection terminal 14. The working electrode 54 and counter electrode 58 remain in an open state with respect to each other (i.e. generally electrically isolated from each other) until an adequate amount of fluid, such as blood, is placed on the test sensor 50. The application of an adequate amount of fluid onto the reagent layer 66 creates an electrochemical reaction that can be detected by the test meter 10.

In a general sense, the test meter 10 applies a predetermined voltage across the working electrode measurement contact pad 70 and the counter electrode measurement contact pad 80 to create a potential difference between the working electrode 54 and counter electrode 58, and then measures the resulting current flow. The magnitude and direction of the voltage is selected based on the electrochemical activation potential for an electrical measurement species to be detected which is generated from the electrochemical reaction of the reagent 66 and applied fluid. For glucose, for example, an applied potential difference typically is between about +100 mV and +550 mV when using a DC potential. When using AC potentials these can be between about +5 mV and +100 mV RMS but can also have larger amplitude depending on the purpose for applying the AC potential. The measured amount of current flow, particularly resulting from a DC potential or sufficiently large amplitude AC potential, is indicative of the concentration of the analyte to be measured. The exact manner in which this process works is beyond the scope of the present invention but known to those skilled in the art. See, for example, U.S. Pat. Nos. 7,727,467; 5,122,244; and 7,276,146, the disclosures of which are hereby incorporated herein by reference.

In order to compensate for the parasitic I-R (current×resistance) drop in the working electrode trace 54a and the counter electrode trace 58a, the test sensor 50 includes the working sense trace 56 and the counter sense trace 60. As set forth above, the working sense trace 56 is connected with the working electrode trace 54a at the distal end 62 of the test sensor 50 and the working sense measurement contact pad 75 at the proximal end 64 of the test sensor 50. The counter sense trace 60 is connected with the counter electrode trace 58a at the distal end 62 of the test sensor 50 and the counter sense measurement contact pad 86 at the proximal end 64 of the test sensor 50.

In one form, during a test procedure a voltage potential is applied to the counter electrode measurement contact pad 80, which will produce a current between the counter electrode 58 and the working electrode 54 that is proportional to the amount of analyte present in the biological sample applied to the reagent layer 66. To ensure that the proper voltage potential is applied to the counter electrode 58, the test meter 10 includes circuitry (not shown) that ensures that a voltage potential (or absolute potential difference) applied to the counter sense trace 60 is the same as the desired voltage potential (or absolute potential difference) at the counter electrode 58. Typically, the test meter 10 will ensure that little to no current will flow through the counter sense trace 60, thereby assuring that the voltage potential seen at the counter electrode 58 corresponds to the desired voltage potential. For a more detailed discussion on the compensation functionality of the working sense trace 56 and the counter sense trace 60 reference can be made to commonly owned U.S. Pat. No. 7,569,126, which is hereby incorporated by reference in its entirety.

The ability to code information directly onto the test strip 50 can dramatically increase the capabilities of the test strip 50 and enhance its interaction with the test meter 10. For example, it is well known in the art to supply the test meter 10 with calibration information or data applicable to multiple lots of test strips 50. Prior art systems have relied on a read-only-memory key (ROM key) that is supplied, for example, with each vial of test strips and is inserted into a corresponding socket or slot in the test meter 10 when the applicable vial of test strips is utilized by the user. Because this process relies upon the user to perform this task, there is no way to guarantee that it is done or if it is, that it is done correctly or each time a new vial of strips is used. In order to remove the possibility of human error or neglect, the present invention provides various manners in which code, such as a code corresponding to preset and pre-stored calibration data, can be placed directly on the test strip 50. This information may then be read by the test meter 10, which has the preset or pre-stored calibration data stored in internal memory, to adjust the test meter 10 so that it can provide precise measurements.

To achieve such encoding, in one embodiment, the test strip 50 includes a secondary or inner resistive element 100 and a primary or outer resistive element 102 that form a base resistance network 104 on the surface of the substrate 52. An end of the secondary resistive element 100 is connected with a secondary resistive element contact pad 103. The primary resistive element 102 has a first end 106, a second end 108 and a predetermined shape or configuration. In one form, the primary resistive element 102 has a serpentine shape or configuration running parallel with the longitudinal axis of the test strip 50. However, it is envisioned that the primary resistive element 102 may have other shapes and configurations in different forms. In one form, the primary resistive element 102 has a predicted resistance value associated with it falling within a predetermined range of resistance values which may be indicative of an attribute of the test strip 50. The resistance value can be measured by the test meter 10 using first and second primary resistive element contact pads 110 and 112 (as defined below).

Figure 3B:
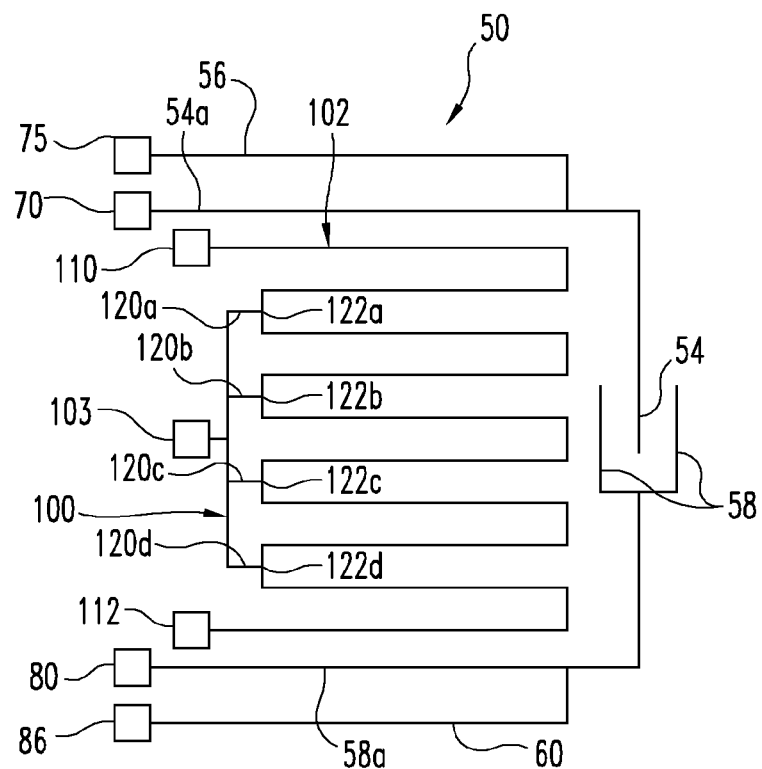

In the embodiment of FIG. 3a, the second end 108 of the primary resistive element 102 is defined by proximal end 78 of the counter electrode trace 58a, and thus contact pad 112 is generally coextensive with counter electrode contact pad 80. Except as otherwise specifically required for a particular use or purpose, it will be understood that whether either end 106 or 108 of the primary resistive element 102 are defined by proximal end 68 of working electrode trace 54a or proximal end 78 of counter electrode trace 58a is a matter of design choice, and the present invention includes embodiments in which ends 106 and 108 are separate and distinct structures from the aspects of the working electrode 54 and counter electrode 58 and the traces 54a, 58a and proximal ends 68, 78 thereof. See, for example, FIG. 3b; in contrast, see description above regarding use of one or both sense traces 56, 60 for purposes of voltage compensation in embodiments in which one or both of contact pads 110, 112 may be coextensive with contact pads 70, 80. The reagent layer 66 has been removed from the remaining figures for ease of reference but it should be appreciated that each test strip 50 disclosed herein will include a reagent layer 66 relevant for the particular analysis desired to be performed.

In particular, the test meter 10 can measure the resistance value of the primary resistive element 102 by applying a voltage across the primary resistive element contact pads 110, 112 and then measuring the amount of current that flows through the primary resistive element 102. In one form, the surface area associated with the primary resistive element 102 is equal to approximately 1372 squares. As such, for illustrative purposes only, for a 50 ηm thick layer of gold, the predicted resistance value associated with the primary resistive element 102 is approximately 2,195.2 Ohms.

Figure 3C:
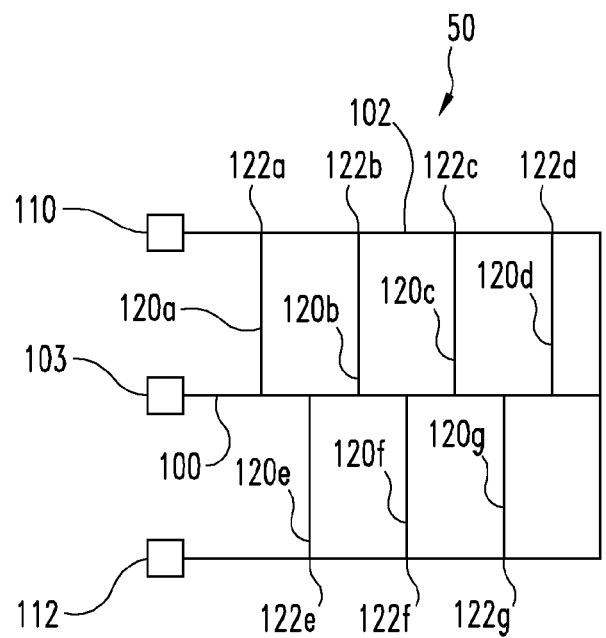

Referring to FIG. 3c, another representative portion of a test strip 50 disclosed herein is illustrated in which the secondary resistive element 100 and primary resistive element 102 have a different predetermined configuration. As set forth in detail below, the secondary resistive element 100 includes a plurality of taps 120a-g that are connected to the primary resistive element 102 at a plurality of predetermined connection points 122a-g. All other features and aspects of this representative embodiment remain the same as described below in connection with the embodiment illustrated in connection with FIGS. 3a, 4 and 5a-g.

Figure 4:
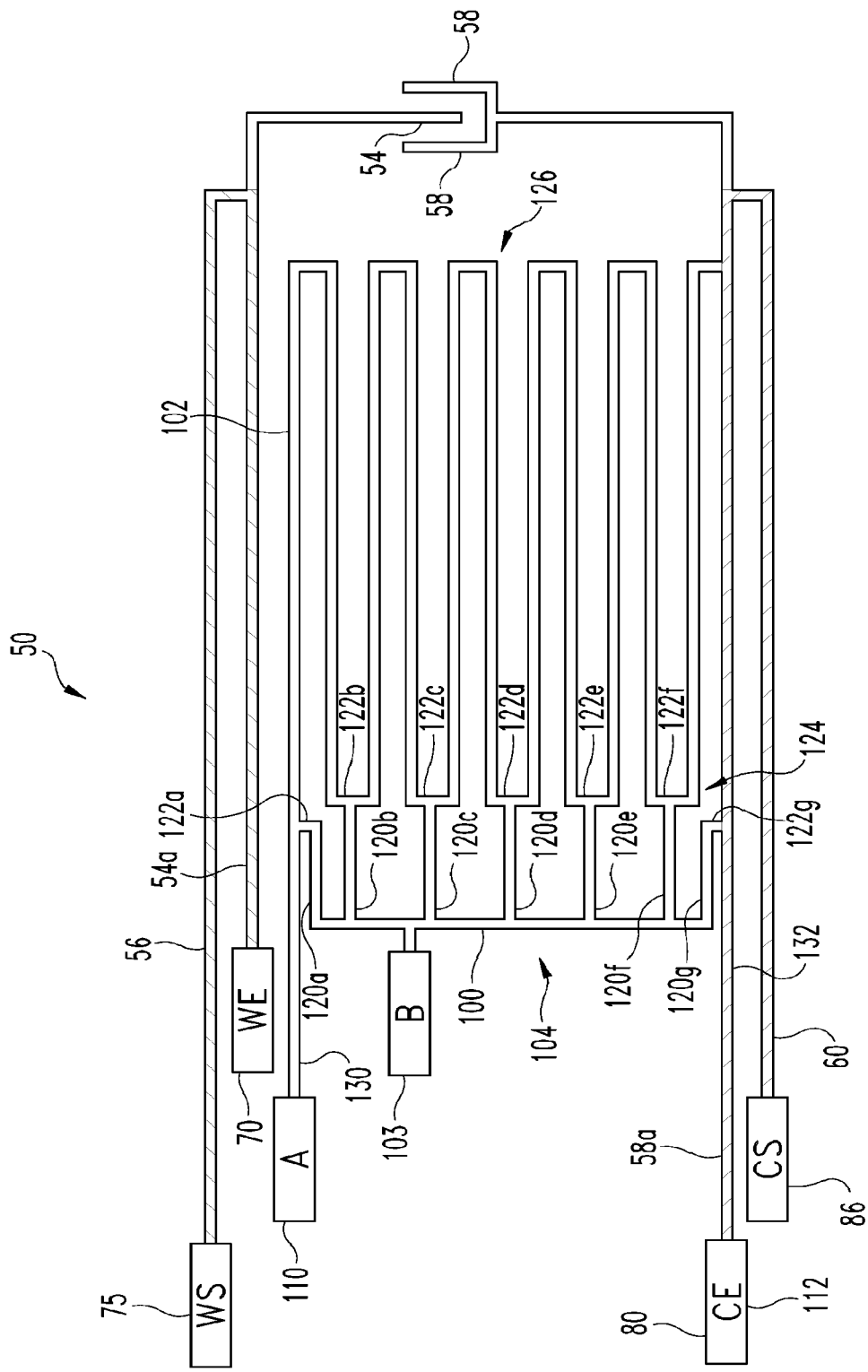
Figure 6:
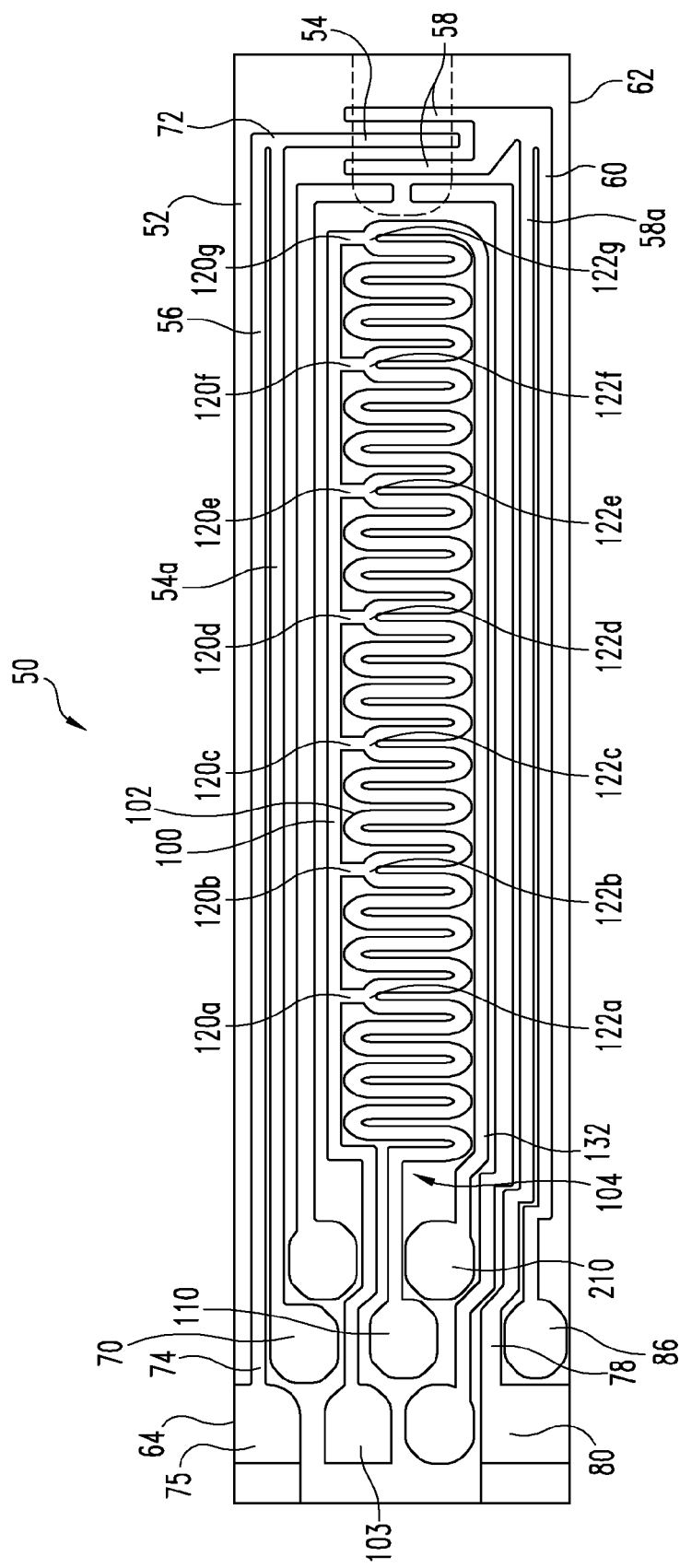
FIG. 6 illustrates another representative test strip for use in measuring the concentration of an analyte of interest in a biological fluid.

Referring to FIG. 4, which illustrates a simplistic view of the electrical aspects of the test strip 50 illustrated in FIG. 3a but without the non-conductive substrate 52, the secondary resistive element 100 includes a plurality of taps 120a-g that are connected to the primary resistive element 102 at a plurality of predetermined connection points 122a-g. In the illustrated form, the primary resistive element 102 has a serpentine shape or configuration which comprises a proximal end 124 and a distal end 126. The taps 120a-g are connected to the connection points 122a-g at the proximal end 124 of the primary resistive element 102. In particular, the taps 120a-g are connected at the proximal ends of each rung of the serpentine configuration. However, it should be appreciated that the taps 120a-g could be connected to the primary resistive element 102 at other locations as well, such as illustrated in FIGS. 3c and 6.

In the form illustrated in FIG. 4, a first end 130 of the primary resistive element 102 is connected with a first primary resistive element contact pad 110. A second end end 132 of the primary resistive element 102 is connected with the counter electrode trace 58a, thereby connecting the second end 132 of the primary resistive element 102 to the counter electrode contact pad 80. As set forth above, in other forms, the second end 132 of the primary resistive element 102 could be connected to a different contact pad 112 other than the counter electrode contact pad 80. See e.g. FIG. 3b.

As illustrated in FIGS. 3a and 4, the base resistance network 104 is initially structured on the non-conductive substrate 52 by the original process that forms the overall electrodes, traces and contact pads on the test strip 50, such as by broad field laser ablation. As set forth in greater detail below, during secondary processing a code may be placed on the test strip 50 by severing all but one of the taps 120a-g of the secondary resistive network 100. As such, the severed taps among 120a-g are placed in an open or non-conductive state while the one remaining tap 120a-g is placed in a closed or conductive state in relation to the primary resistive element 102. Severing may be accomplished by manual or other means, such as ablation or scribing with an appropriate laser.

During manufacturing, once a respective lot of test strips 50 is produced having the base resistance network 104 formed thereon, one or more pertinent attributes of the lot are determined in order to encode each test strip 50 in the lot accordingly for communicating the attribute(s) to the test meter 10. For example, in one embodiment one or more of the test strips 50 from the lot are tested with a target analyte having a known concentration. The test results typically indicate an attribute comprising calibration data, such as values for slope and intercept for an algorithm based on a generally linear relationship for measurement of the target analyte, which calibration data should be employed by the test meter 10 in a final measurement determination that uses the test strips 50. In a secondary processing of the remaining lot of test strips 50, the base resistance network 104 is modified in order to place a code on the test strip 50 that is associated with the calibration data for that lot of test strips 50.

In one form, the attribute comprising calibration data for the lot of test strips 50 permits the test meter 10 to automatically adjust itself to provide precise measurements of the target analyte. In particular, the resistive network that is created on the test strip 50 during secondary processing is used to convey information to the test meter 10 related to strip performance such as algorithm slopes and product type. In one particular embodiment, the secondary resistive element 100 is modified to exhibit only one of a plurality of possible states, wherein each state comprises at least a portion of the code on the test strip 50.

According to one aspect, the base resistance network 104 is formed such that all taps 120a-g are in a closed state by manufacturing default. The default state conveys to the meter 10 a so-called nominal code for a particular test strip type, e.g. a nominal slope and/or intercept values for a linear correlation algorithm. Each of the plurality of possible other states created by later severing or opening all but one of the taps 120a-g (detected as set forth further below) may then convey incremental adjustment values to the nominal code or to values calculated from the algorithm using the nominal code. For example, for taps 120a-g there are seven possible states in which only one tap remains closed. Each such state may represent a positive or negative factor (e.g. a multiplier) which when conveyed to meter 10 is employed by the meter to adjust calculated output upwardly or downwardly depending on how the particular strip lot is evaluated compared to the nominal code. Thus, states 1-3 may represent multipliers −1%, −2%, and −3% respectively, while states 4-7 may represent multipliers +1%, +2%, +3% and +4% respectively. Such embodiments provide an alternative to the states each representing a set of code values (e.g. slope and intercept) pre-stored in the meter 10 that are then employed by the meter in the correlation algorithm.

In an alternative form, all of the taps 120a-g may be ablated or placed in an open state during primary processing. In this form, a respective tap 120a-g is placed in a closed state during secondary processing depending on the test results of the lot of test strips 50. The tap 120a-g that is required to be placed in the closed state may be placed in the closed state during secondary processing by ink jet printing, soldering, drop dispensing, screen printing, conductive taping, and so forth. In other alternative forms, the masks used to form the test strips 50 may be formed already having one tap 120a-g placed in a closed state and the remaining in an open state thereby eliminating the need for secondary processing of the test strips 50.

Figure 5A:
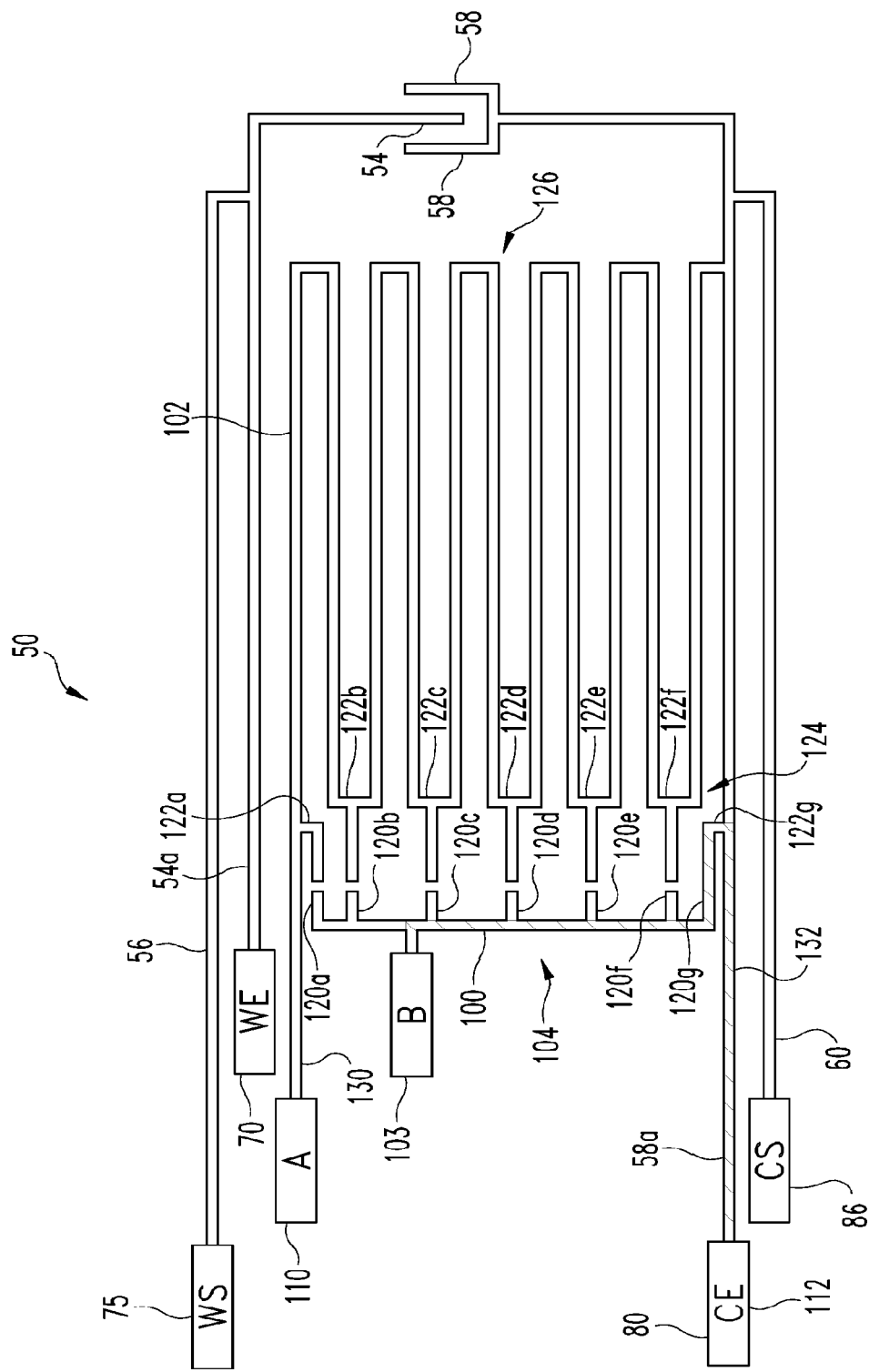
FIGS. 5a-g illustrate a portion of the test strip illustrated in FIG. 3a having a plurality of ablated taps.
Figure 5B:
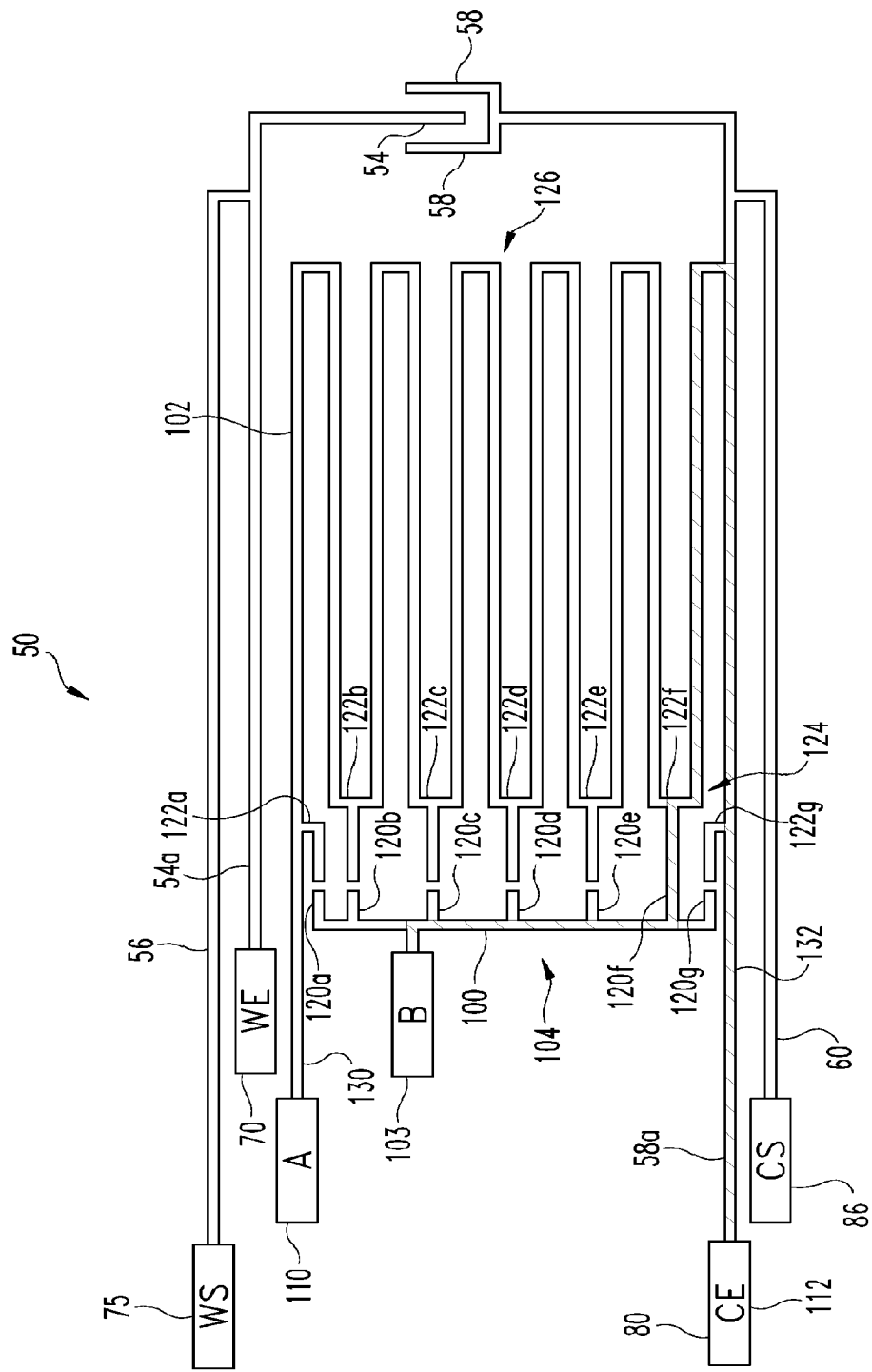
Figure 5C:
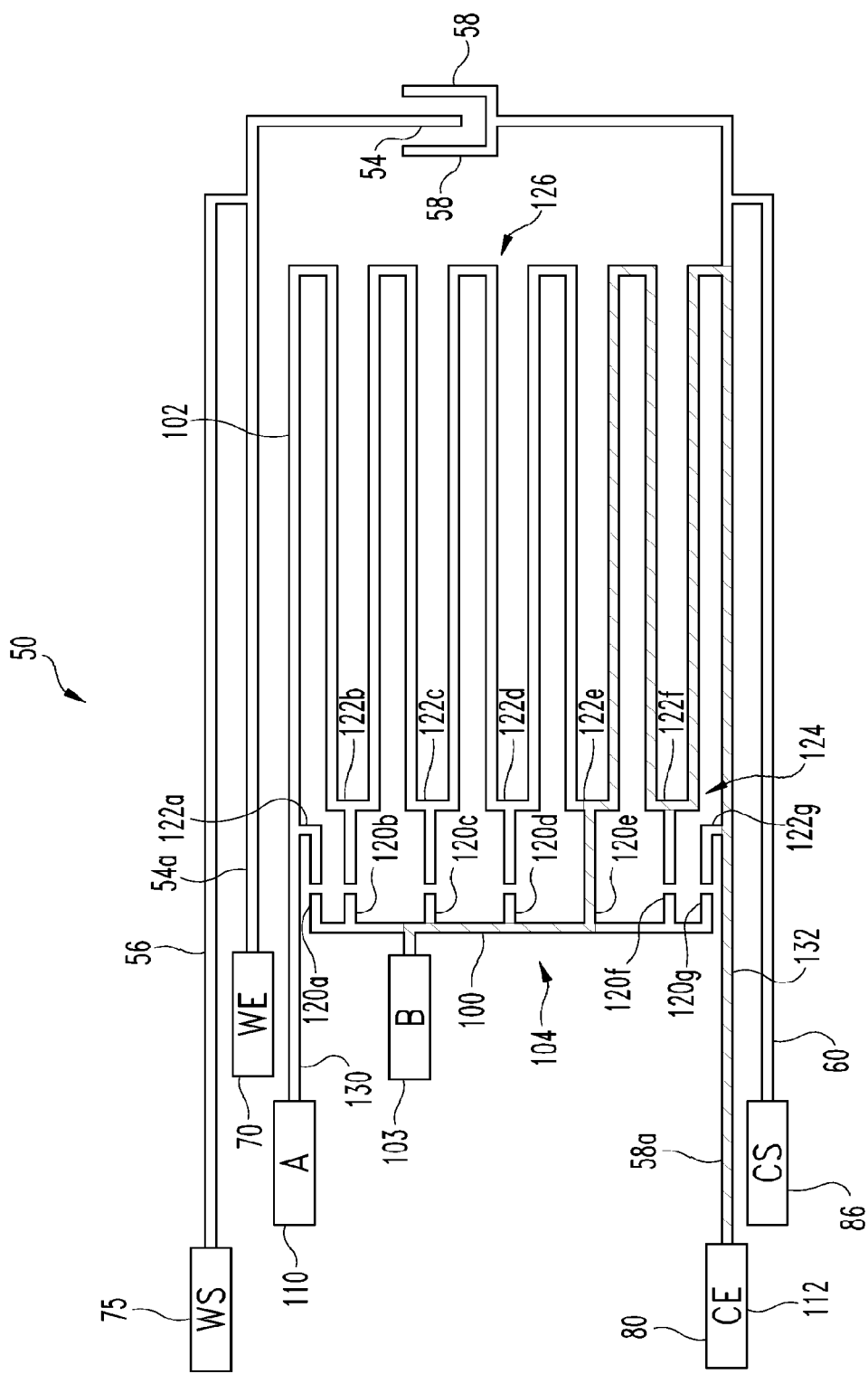
Figure 5D:
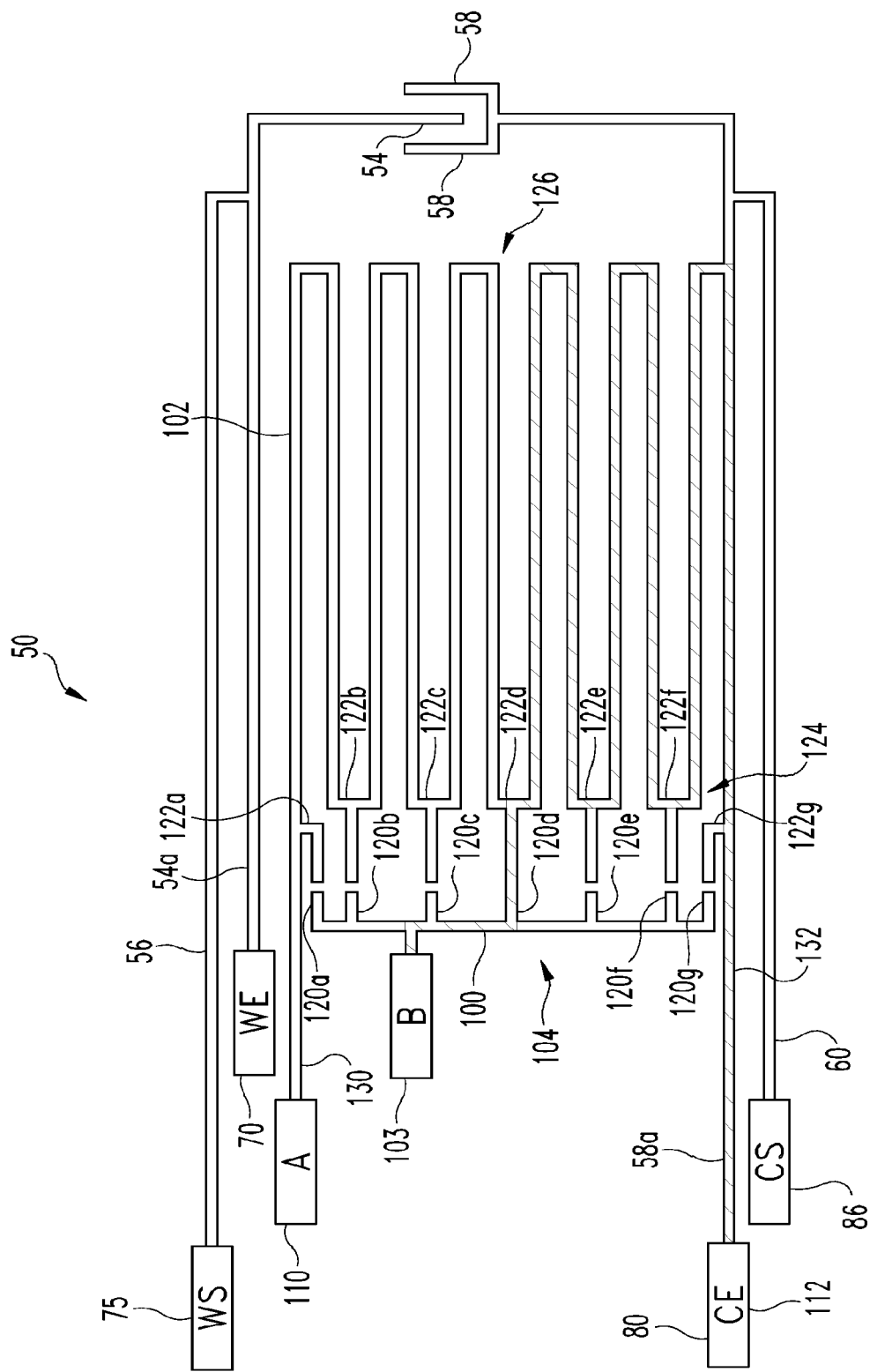
Figure 5E:
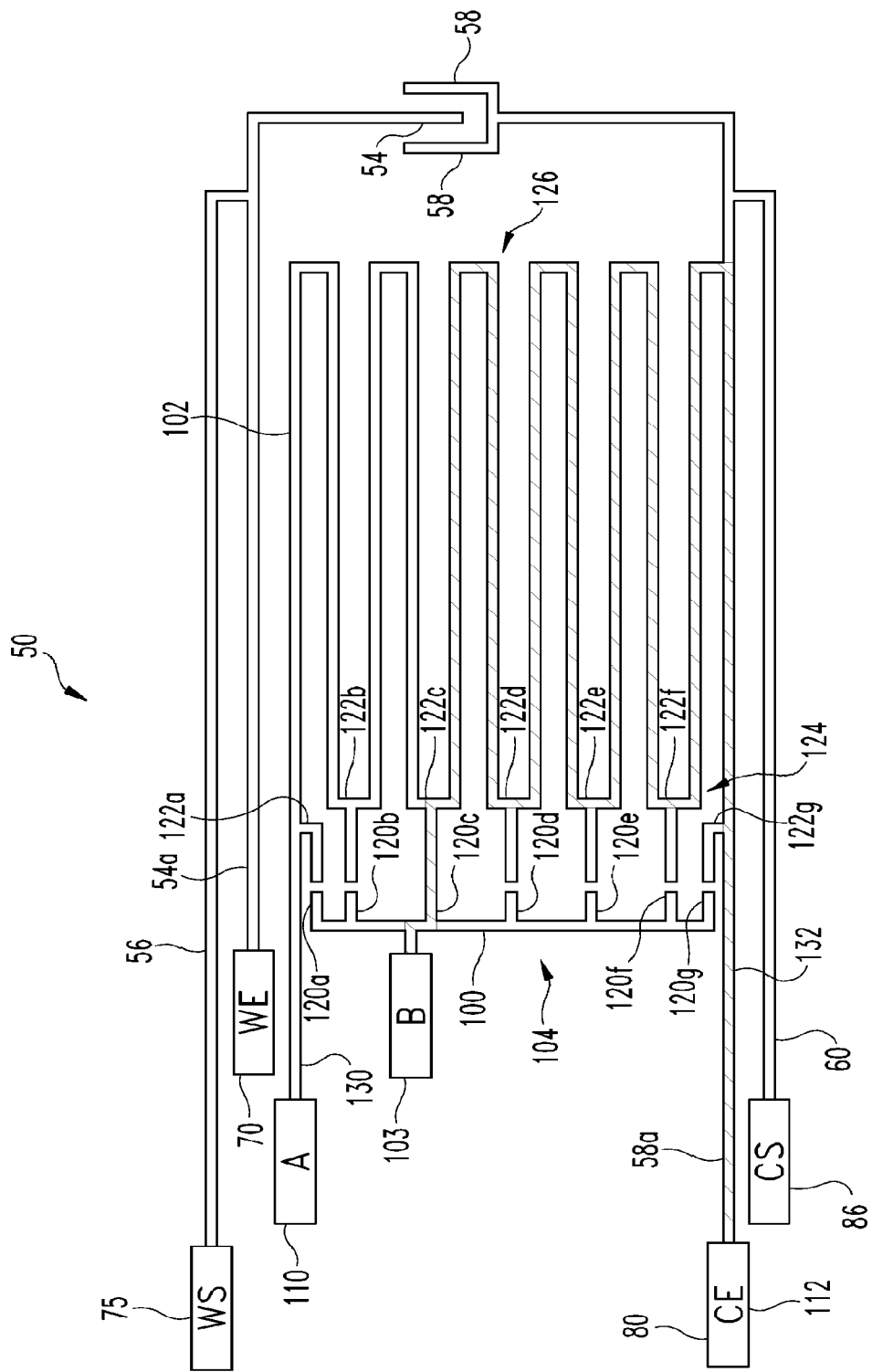
Figure 5F:
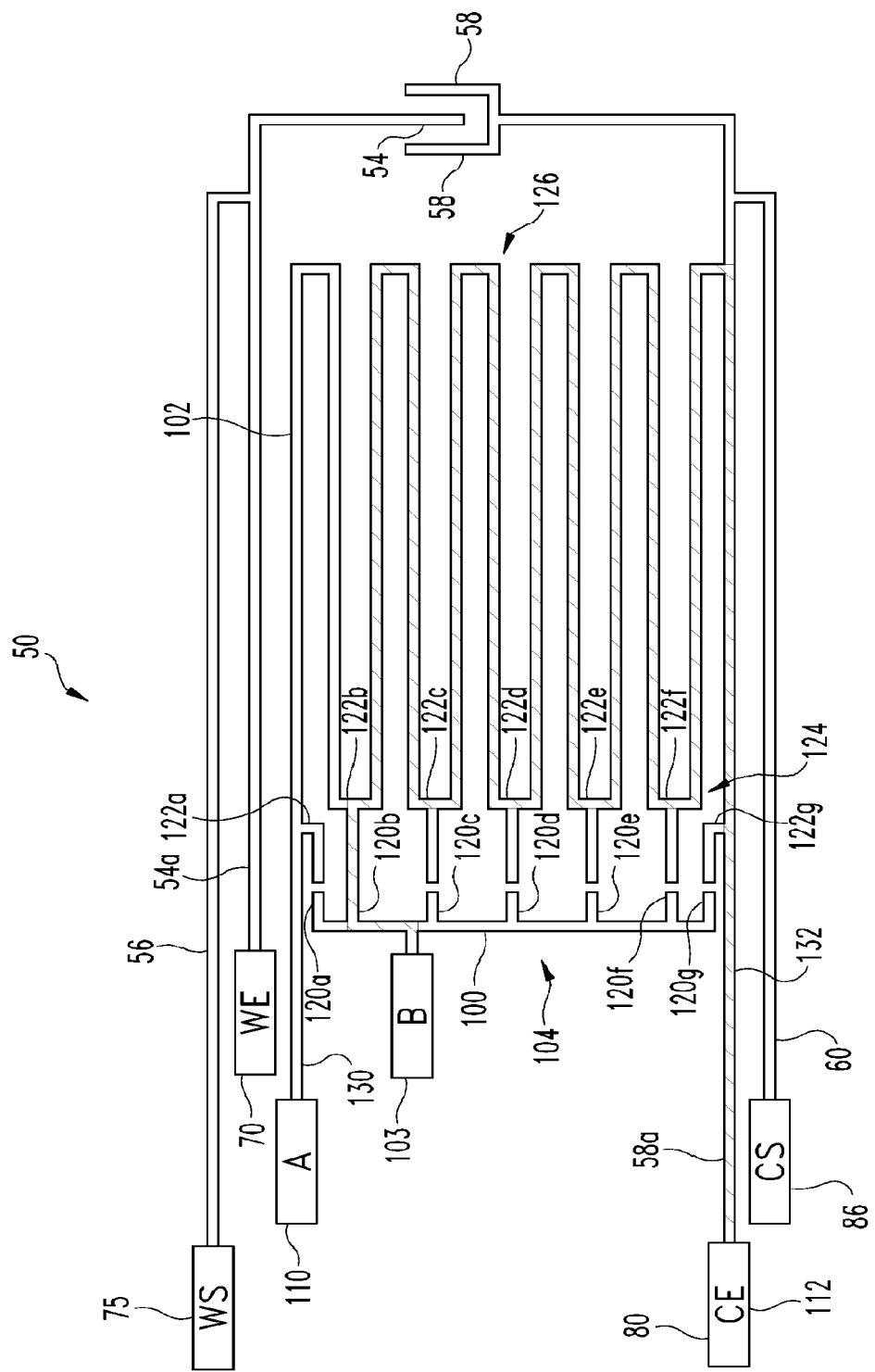
Figure 5G:
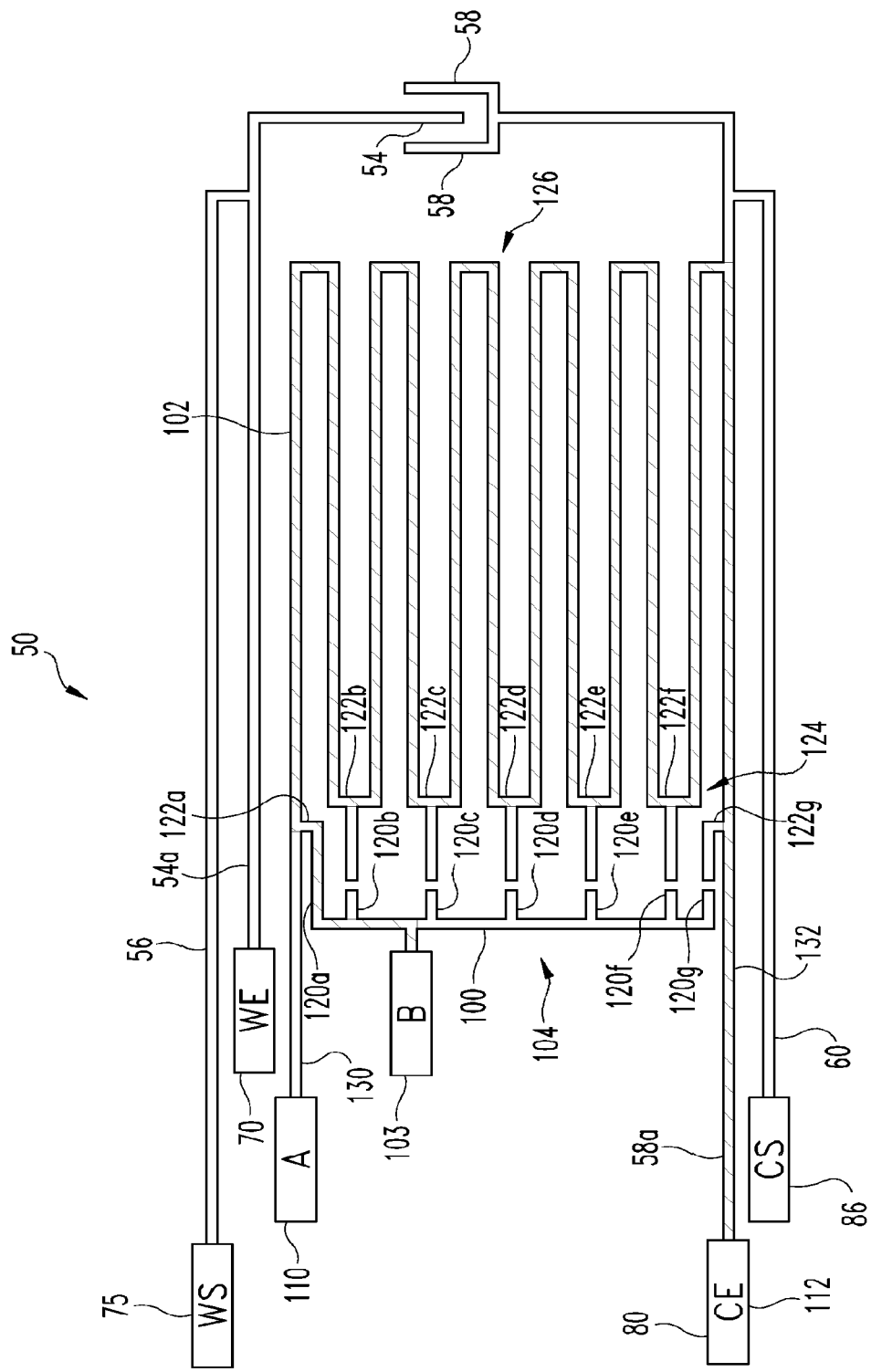

Referring to FIG. 5a, during secondary processing of the test strips 50, the base resistance network 104 is modified such that code information indicative of an attribute associated with the test strip 50 is placed on the test strips 50. As set forth above, the modified base resistance network 104 can be utilized to transfer basic information to the test meter 10 related to strip performance such as algorithm slopes and product type. As illustrated in FIG. 5a, during secondary processing all but one of the taps 120a-g, which are taps 120a-f in this illustrative example, have been ablated by a laser thereby defining a first state (State 1) that the test strip 50 may be produced in. In particular, in State 1 only tap 120g remains connected to the primary resistive element 102 at location 122g thereby defining a first unique resistive path for secondary resistive element 100 through a portion of the primary resistive element 102. The ablated taps 120a-f are thereby placed in an open state and the non-ablated tap 120g is in a closed state thereby allowing current to flow through the secondary resistive element 100, and into a select portion of the primary resistive element 102.

As illustrated in FIG. 5a, a first unique resistive path is defined from the secondary resistive element contact pad 103 through the secondary resistive element 100 including the non-ablated tap 120g and a portion of the primary resistive element 102 between location 122g and the contact pad 112 at the second end 132. The first unique resistive path is defined at least in part by the non-ablated tap 120g and a portion of the primary resistive element 102. In one form, for purposes of illustration, in State 1 the first unique resistive path has a resistance value associated with it of approximately 38.4 Ohms. For illustrative clarity, the first unique resistive path is shown in FIG. 5a between contact pads 103 and 112 in hashed line shading.

As with all of the forms discussed below, the resistance value associated with the first unique resistive path can be measured by the test meter 10 using the secondary resistive element contact pad 103 and the contact pad 112 (which as illustrated is co-extensive with counter electrode contact pad 80). In particular, the resistance value can be measured by the test meter 10 by applying a predetermined voltage across the secondary resistive element contact pad 103 and the contact pad 112 and then by measuring the resulting current flow through the first unique resistive path and then calculating resistance according to Ohm's Law, R=V/I.

Alternatively, a second unique resistive path is defined by State 1 from the secondary resistive element contact pad 103 through the secondary resistive element 100 including the non-ablated tap 120g and a portion of the primary resistive element 102 between location 122g and the primary resistive element contact pad 110 at first end 130. In this alternative form, the second unique resistive path has a resistance value associated with it of approximately 2182.4 Ohms. As with all of the forms discussed below, the resistance value associated with the second unique resistive path for each state can be measured by the test meter 10 using the secondary resistive element contact pad 103 and the primary resistive element contact pad 110. The resistance value can be measured by the test meter 10 by applying a predetermined voltage across the secondary resistive element contact pad 103 and the primary resistive element contact pad 110 and then by measuring the resulting current flow through the second unique resistive path and calculating resistance as described above.

Referring to FIGS. 5b-5g, additional states (e.g. States 2-7) each including first and second unique resistive paths for each state may be defined on the basis of which tap 120a-120f remains unablated. In each instance, a first unique resistive path is defined from secondary resistive element contact pad 103 through the secondary resistive element 100 including the particular non-ablated tap 120f-120a (such as shown in FIGS. 5b-5g, respectively) and a portion of the primary resistive element 102 between particular location 122f-122a (respectively) and contact pad 112 at second end 132. (For illustrative clarity, the first unique resistive path in each of FIGS. 5b-5g is shown between contact pads 103 and 112 in hashed line shading.) Conversely, in each instance a second unique resistive path is defined from secondary resistive element contact pad 103 through the secondary resistive element 100 including the particular non-ablated tap 120f-120a (such as shown in FIGS. 5b-5g, respectively) and a portion of the primary resistive element 102 between particular location 122f-122a (respectively) and contact pad 110 at first end 130.

For purposes of further illustration, Table 1 sets forth exemplary resistance values associated with the first and second unique resistive paths ("URP") defined for each of States 1-7 shown in FIGS. 5a-5g, in which the paths are formed from gold having 50 ηm thickness. It will be understood that other materials, thicknesses and path configurations will have different associated resistance values for each state.

TABLE 1

| | Associated Resistance Values (Ohms) | | | | | | |
|---|---|---|---|---|---|---|---|
| | State 1 | State 2 | State 3 | State 4 | State 5 | State 6 | State 7 |
| URP #1 | 38.4 Ohms | 332.8 Ohms | 699.2 Ohms | 1068.8 Ohms | 1440 Ohms | 1812.8 Ohms | 2182.4 Ohms |
| URP #2 | 2182.4 Ohms | 1812.8 Ohms | 1440 Ohms | 1068.8 Ohms | 699.2 Ohms | 332.8 Ohms | 38.4 Ohms |

As set forth above with respect to FIGS. 5a-g, the test strip 50 disclosed herein can be configured during manufacturing to transmit a minimum of seven (7) basic states of product performance and attribute information from the comparative analysis of resistance traces on the test sensor strip 50. Although discrete resistance values have been set forth above in the illustrative forms and as described further above with regard to predicted resistance values, it should be appreciated that in some embodiments these values will vary somewhat because of variances in the manufacturing process. As such, each state that the test strip 50 may be manufactured in during secondary processing will typically fall within a range of resistance values. Thus, in one embodiment, each discrete range of resistance values rather than the discrete resistance values themselves, will correspond to a state of the test strip 50. For example, in one form, the resistance value of the first unique resistive path in State 1 could fall within a range of 20-150 Ohms, in State 2 could fall within a range of 310-450 Ohms, and so forth.

The method used to measure resistance and other factors, such as the temperature of the test strip 50 and the internal electronics configuration of test meter 10, can also affect the resistance measured by the test meter 10 and thus minimize the size of each discrete range of resistances that may be used. For example, the measured resistance may also include the resistance of at least one switch internal to the test meter 10, where the resistance of the switch varies depending on the temperature of the switch and manufacturing tolerances. In one embodiment, the internal switch resistances as well as contact resistances (i.e. the resistance from the contact of a contact pin of the meter to a particular contact pad) are accounted for and thus automatically compensated in the calculation of resistance values for each primary resistive element 102 and secondary resistive element 100.

In other forms, the test meter 10 can be configured to determine the state of the test strip 50 in a manner in which the resistance values are ratioed, or proportionally compared, with at least one other resistance value on the test strip 50. As such, the test meter 10 can be configured to measure the resistance value of the first or second unique resistive path through the secondary resistive element 100 and primary resistive element 102 and then compare it to another measured resistive value of the test strip 50. For example, the test meter 10 could ratio the measured resistance value of the first or second unique resistive path of the secondary resistive element 102 and primary resistive element 102 against the measured resistance of one or more of the primary resistive element 102, the working resistance loop, and the counter resistance loop to determine the state of the test strip 50.

Referring back to FIG. 3a, in another form the test strip 50 is provided with an optical two dimensional code 200 on the proximal end 64 of the test strip 50. In some forms, the test meter 10 is provided with an optical code reader (not shown) that allows the test meter 10 to read the optical two dimensional code 200. Additional information that may be provided by the optical two dimensional code 200 can be product expiration date, product identification (countries or regions), intercepts of blood and control solutions, strip lot identification, and other features.

Referring to FIG. 6, another representative form of a test strip 50 is disclosed that may incorporate the features disclosed herein. In this form, wherein like-numbered elements correspond to the same features, the primary resistive element 102 is formed having a different serpentine shape. In particular, instead of running parallel to the longitudinal axis of the test strip 50, the serpentine configuration runs perpendicular to the longitudinal axis of the test strip 50. This configuration also modifies where the connection points 122a-g of the secondary resistive element 100 connect to the primary resistive element 102. In addition, the taps 120a-g of the secondary resistive element 100 are oriented perpendicular to the longitudinal axis of the test strip 50.

In this form, the second end 132 of the primary resistive element 102 is connected with a second primary resistive element contact pad 210. In the previous form illustrated in FIG. 3a, the second end 132 of the primary resistive element 102 is formed with the counter electrode trace 58a (with counter electrode contact pad 80 shown as co-extensive with contact pad 112). However, as discussed above, the second end 132 of the primary resistive element 102 can be connected with contact pad 210 separate from counter electrode trace 58a and counter electrode contact pad 80, as illustrated in FIG. 6. As with the form illustrated in FIG. 3a, during secondary processing of the test strips 50, all but one of the taps 120a-g is ablated to place the test strip 50 in a predefined state (e.g.—States 1-7). In this form, the test meter 10 is configured to determine the resistance of the primary resistive element 102 by using the first primary resistive element contact pad 110 and the second primary resistive element contact pad 210. All other features remain the same as discussed in connection with the form illustrated in FIG. 3a.

Figure 7:
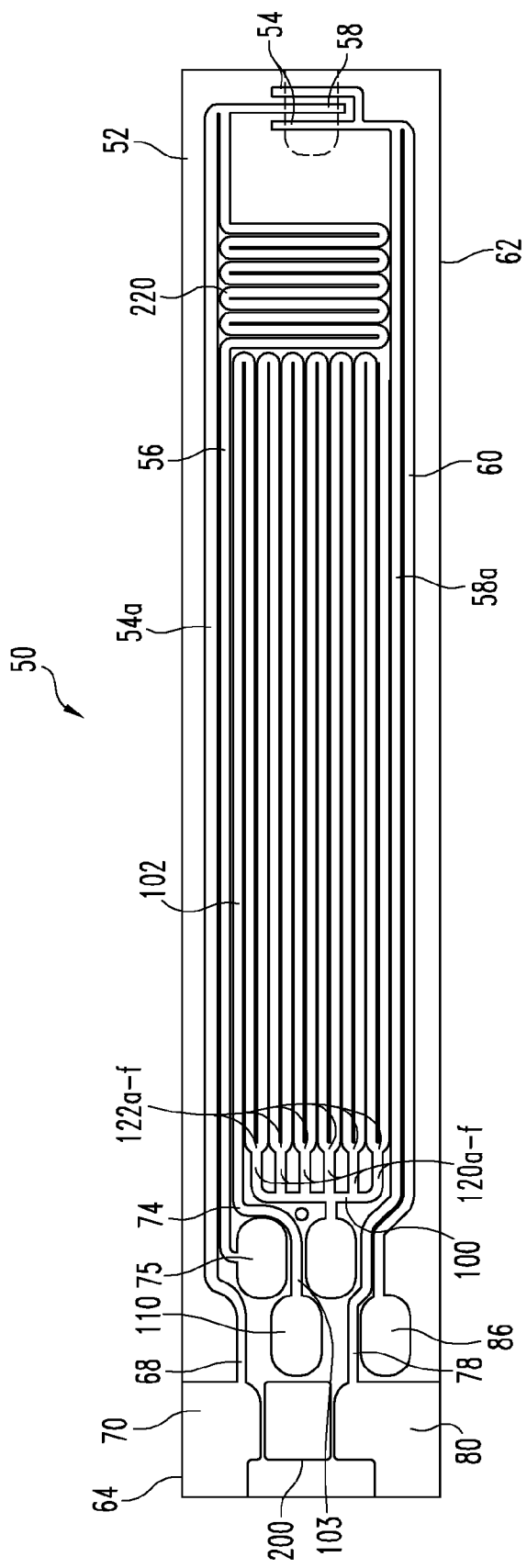
FIG. 7 illustrates another representative test strip for use in measuring the concentration of an analyte of interest in a biological fluid.

Referring to FIG. 7, another form of a test strip 50 is illustrated that includes a working sense serpentine 220 in the working resistance loop. In this form, the working sense serpentine 220 is used to code additional information on the test strip 50 related to an attribute of the test strip 50. As depicted, the working sense trace 56 has been formed to include the working sense serpentine 220, which in the illustrated embodiment is located on the distal end 62 of the test strip 50. The working sense serpentine 220 allows the working resistance loop to be selectively formed having a predetermined resistance value that falls within a range of resistances. The resistance value can vary depending on the presence or absence of working sense serpentine 220, and in the present thereof then also depending on the width, length, thickness and conductive material used to form the working sense serpentine 220 on the test strip. The resistance value of the working resistance loop can be measured by the test meter 10 by applying a predetermined voltage across the working sense measurement contact pad 75 and the working electrode measurement contact pad 70 and then measuring the resulting current flow and calculating resistance accordingly.

Figure 8:
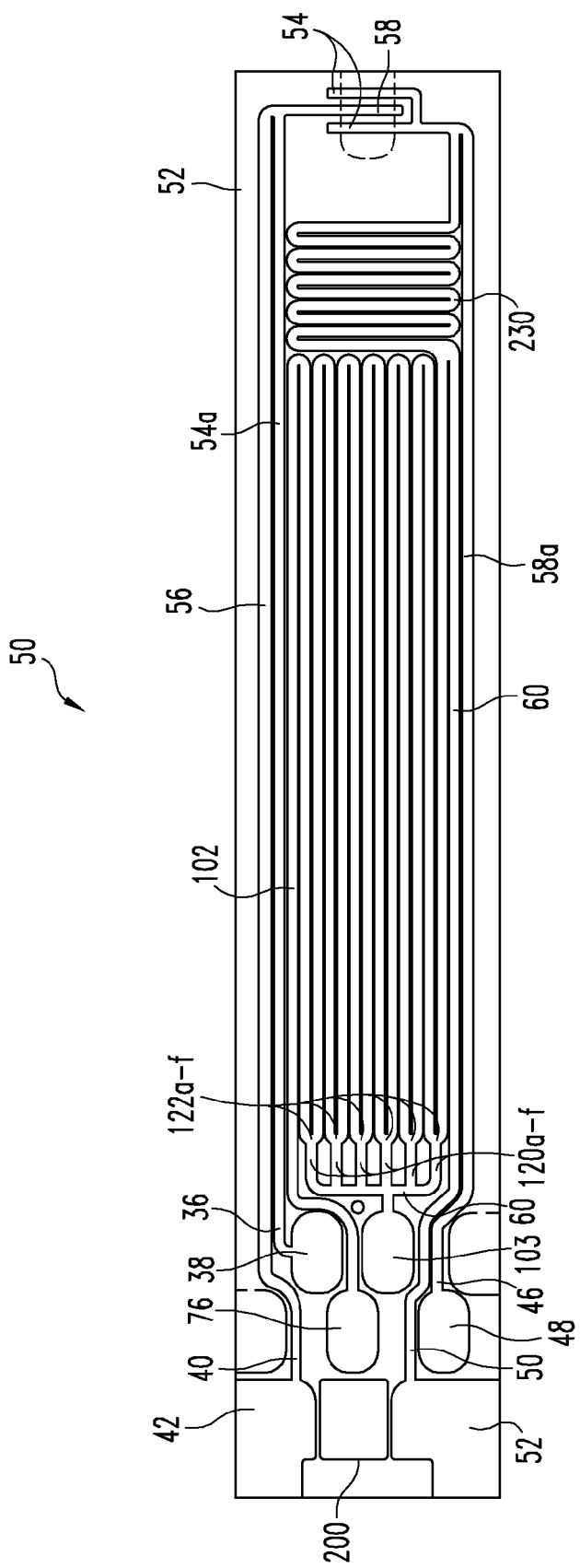
FIG. 8 illustrates another representative test strip for use in measuring the concentration of an analyte of interest in a biological fluid.

Referring to FIG. 8, another form of a test strip 50 is illustrated that includes a counter sense serpentine 230 in the counter resistance loop. As with the form illustrated in FIG. 7, in this form the counter sense serpentine 230 is used to code additional information on the test strip 50 related to an attribute of the test strip 50. The counter sense trace 60 has been formed to include the counter sense serpentine 230, which in the illustrated embodiment is located on the distal end of the test strip 50. The counter sense serpentine 230 allows the counter resistance loop to be selectively formed having a predetermined resistance value that falls within a range of resistances. The resistance value of the counter resistance loop can be measured by the test meter 10 by applying a predetermined voltage across the counter sense measurement contact pad 86 and the counter electrode measurement contact pad 80 and then measuring the resulting current flow.

Figure 9:
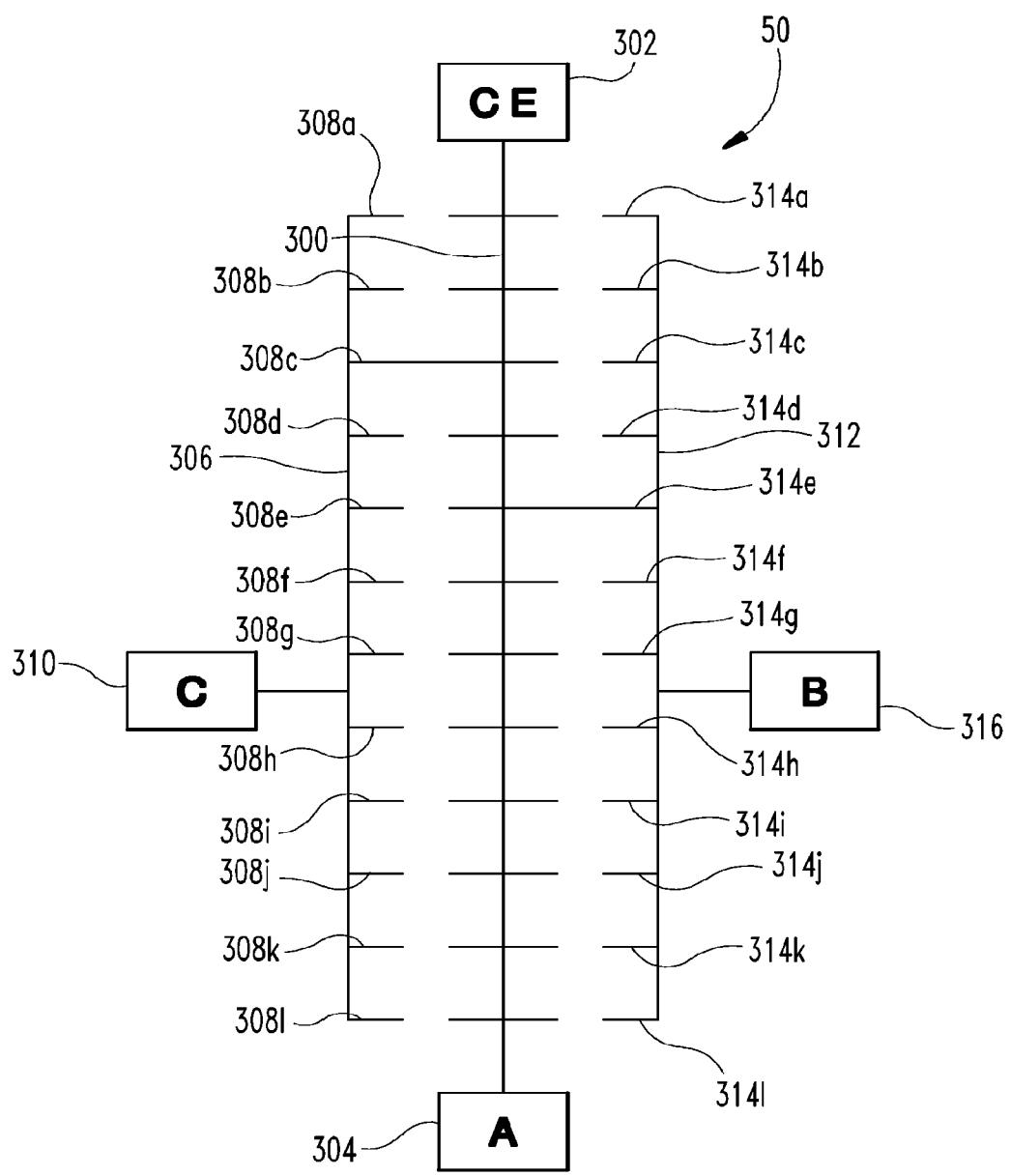
FIG. 9 illustrates a portion of another representative test strip for use in measuring the concentration of an analyte of interest in a biological fluid.
Figure 10:
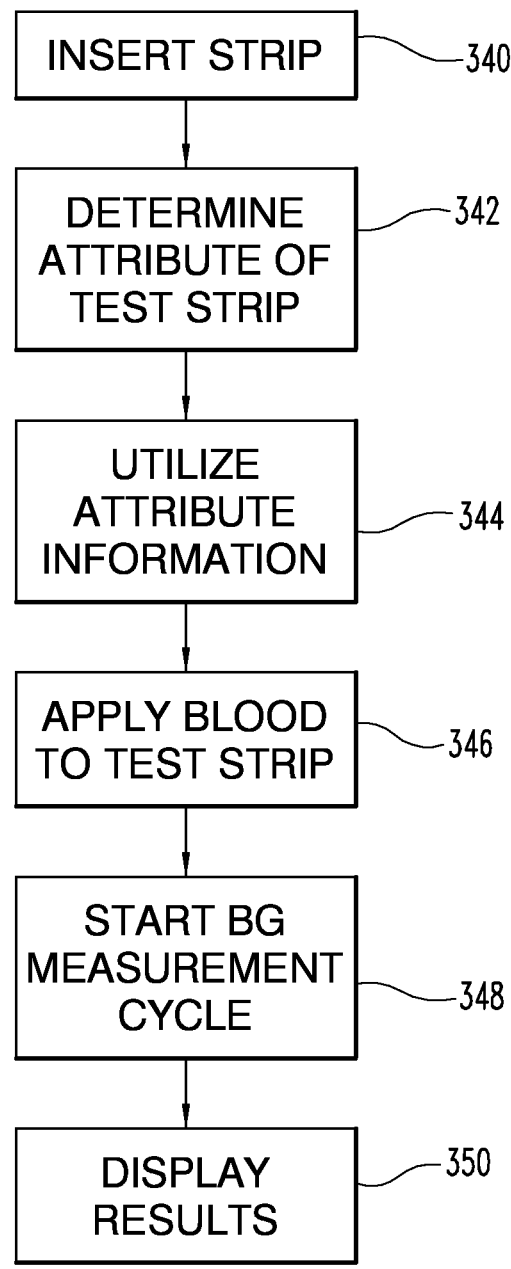
FIG. 10 is a flow diagram of a representative process used to measure an analyte in a biological fluid.

Referring to FIG. 9, an alternative form of a test strip 50 that is configured to test for the concentration of an analyte is disclosed that is encoded with information pertaining to at least two attributes of the test strip 50. In this form, a first resistive element 300 is defined between a first contact pad 302, such as, for example, a counter electrode contact pad, and a second contact pad 304. As illustrated, a second resistive element 306 including a first set of taps 308a-1 is connected with the first resistive element 300. As with the previous forms, all but one of the first set of taps 308a-1 has been ablated thereby placing taps 308a-b and 308d-1 in an open state. Tap 308c is in a closed state thereby defining a first unique resistive path from a third contact pad 310 through the second resistive element 306 and at least a portion of the first resistive element 300 to the first contact pad 302. A second unique resistive path is also defined from the third contact pad 310 through the second resistive element 306 and a least a portion of the first resistive element 300 to the second contact pad 304. In this form, up to twelve (12) states can be defined by the first and second unique resistive paths depending on which tap 308a-1 is placed in the closed state.

A third resistive element 312 including a second set of taps 314a-1 is also connected with the first resistive element 300. Once again, all but one of the second set of taps 314a-1 has been ablated thereby placing taps 314a-d and 314f-1 in an open state. For illustrative purposes only, tap 314e has been placed in a closed state thereby defining a third unique resistive path from a fourth contact pad 316 through the third resistive element 312 and at least a portion of the first resistive element 300 to the first contact pad 302. A fourth unique resistive path is also defined from the fourth contact pad 316 through the third resistive element 312 and at least a portion of the first resistive element 300 to the second contact pad 304. In this form, up to twelve (12) states can be defined by the third and fourth unique resistive paths depending on which tap 314a-1 is placed in the closed state. The number of taps 314a-1 associated with the third resistive element 312 dictates how many states may be defined on the test strip 50. In other forms, additional resistive elements, contact pads and taps could be placed on the test strips to encode additional information on the test strips.

Referring to FIGS. 5a-g and 10, a general description of a representative process that allows the test meter 10 to measure the concentration of an analyte in a biological fluid is set forth. The process begins by inserting a test strip 50 (step 340) into the test meter 10. In this form, the test meter 10 is configured to automatically turn on once a test strip 50 is inserted into the test meter 10. At this point, the test meter 10 is configured to measure the conductivity of the base resistance network 104 to ascertain at least one attribute associated with the test strip 50, which is represented at step 342. In one form, the test meter 10 is configured to apply a predetermined voltage across the secondary resistive element contact pad 103 and one of the contact pads 110, 112 (depending on whether the first or second unique resistive path is being queried) and then measure the resulting current flow to calculate resistance and determine the state of the test strip 50 (e.g. one of States 1-7). As set forth above, the state of the test strip 50 is determined as a function of a first resistance value that is associated with either the first or second unique resistive path that defines the secondary resistive element 100.

In other forms, the test meter 10 is also configured to determine a second resistance value associated with the primary resistive element 102. In this form, the test meter 10 is configured to apply a predetermined voltage across the primary resistive element contact pads 110, 112 and then measure the resulting current flow and calculate resistance accordingly. The test meter 10 then calculates a ratio of the first resistance value (i.e. the resistance associated with the selected unique resistive path) and the second resistance value (i.e. the resistance associated with the primary resistive element 102) and then correlates this ratio to an attribute of the test strip 50 such as by a look-up table pre-stored in the memory of test meter 10. As set forth above, in one form the attribute that the test meter 10 determines during this process correlates to an algorithm slope and intercept determined for the particular lot of the test strip 50.

Once the test meter 10 determines the attribute, the test meter 10 is configured to automatically utilize the information relating to the attribute, which is represented at step 344. For example, in one embodiment the test meter 10 is instructed to perform a particular type of test specific to the test strip 50 that has been inserted; or the test meter 10 calibrates the meter according to pre-stored calibration information for the lot of test strips. The test meter 10 is configured as a function of the attribute that is determined at step 342. Thus, in the calibration embodiment, depending on the determined state of the test strip 50, the test meter 10 includes algorithm slopes stored in memory that allow the test meter 10 to be adjusted for the particular type of test strip 50 that has been inserted into the test meter 10. This allows the test meter 10 to provide more precise results without requiring the user to have to interact with the test meter 10 during the testing process.

After the test meter 10 is configured according to the coded attribute information, the measurement sequence is ready to begin such as by prompting a user to apply blood, for example, to the test strip 50, which is represented at step 346. Once blood has been applied to the test strip 50, the test meter 10 then begins the blood glucose measurement cycle, which is represented at step 348. After the test meter 10 performs the blood glucose measurement cycle, the test meter is configured to display the results on the display 16 (step 350). It should be appreciated that this illustrative example is just a basic example and that the test meter 10 is configured to do many other tasks as well. For example, the test meter 10 can be configured to store the test results in memory so that the user can view test results from the past.

As used herein, the term ablate should be broadly construed to mean to remove or destroy, which can be done by, for example, cutting, abrading, or vaporizing. In one form, at least a portion of the taps 120a-g is ablated by a laser, which can be a diode-pumped solid state laser or a fiber laser. In an illustrative form, the diode-pumped solid state laser is a 355 nanometer diode-pumped solid state laser and the fiber laser is a 1090 nanometer fiber laser.

Illustrated embodiments of the secondary resistive element 100 show that seven states are possible depending on which one of taps 120a-g are left closed. It will be well understood by those of ordinary skill in the art that the number of states may be increased or decreased as desired or needed by adding or removing taps 120 from the design for the base resistance network 104, with corresponding increase or decrease in the number of predetermined connection points 122.

Although embodiments of the invention have been described using specific terms, such description is for illustrative purposes only, and it is to be understood that changes and variations obvious to the skilled artisan are to be considered within the scope of the claims that follow and their equivalents.

What is claimed is:
1. An analyte test sensor strip, comprising:
a non-conductive substrate; a plurality of measurement electrodes formed on the non-conductive substrate, wherein the plurality of measurement electrodes comprises at least a working electrode and a counter electrode;
a reagent bridging the working electrode and the counter electrode;
an information circuit formed on the non-conductive substrate, the information circuit comprising:

a primary resistive element having a first end and a second end having a predetermined configuration between the first and second ends, wherein the primary resistive element has a resistance falling within a first predetermined range, and a secondary resistive element between the first end of the primary resistive element and a third end, wherein the secondary resistive element comprises a plurality of closed taps, wherein the closed taps selectively connect the third end with the primary resistive element each at a predetermined location thereby defining a plurality of selectable, unique resistive paths between the first end and the third end through at least a portion of the primary resistive element, wherein each of the plurality of selectable, unique resistive paths has a second resistance falling within a second predetermined range; and a plurality of contact pads formed on the non-conductive substrate, wherein at least a first contact pad of the plurality of contact pads is connected to the first end of the primary resistive element, a second contact pad of the plurality of contact pads is connected to the second end of the primary resistive element, and a third contact pad of the plurality of contact pads is connected to a portion of the secondary resistive element;

wherein a ratio of the first resistance and the second resistance selectively correlates to an attribute of the analyte test sensor strip.

2. The analyte test sensor strip of claim 1, wherein the predetermined configuration of the primary resistive element comprises a serpentine configuration having a plurality of proximal ends and a plurality of distal ends.

3. The analyte test sensor strip of claim 2, wherein each of the plurality of closed taps of the secondary resistive element is connected to a respective proximal end of the primary resistive element.

4. The analyte test sensor strip of claim 1, wherein each of the plurality of closed taps can be selected as a function of an attribute of the analyte test sensor strip.

5. The analyte test sensor strip of claim 1, further comprising an optical code on the non-conductive substrate.

6. The analyte test sensor strip of claim 5, wherein the optical code contains at least one informational attribute associated with the analyte test sensor strip selected from the group consisting of a product expiration date, a product identification, intercepts of blood and control solution information, a strip lot identification, and a strip performance algorithm identifier.

7. A method of measuring an analyte concentration in a sample of fluid, comprising:

inserting the analyte test sensor strip of claim 1 into a test meter, wherein the working electrode, the counter electrode, the primary resistive element, and the secondary resistive element connect to the test meter through the plurality of contact pads;

determining an attribute associated with analyte test sensor strip as a function of a measurement associated with at least the resistance value associated with at least one of the plurality of selectable, unique resistive paths;

configuring the test meter as a function of the attribute; applying the sample of fluid and measuring the analyte concentration; and displaying a measurement of the analyte concentration on a display of the test meter;

wherein the primary resistive element has a primary element resistance value and the attribute is determined as a function of a resistance ratio determined by comparing the resistance value of at least one of the plurality of selectable, unique resistive paths with the primary element resistance value.

8. The method of claim 7, wherein an end of the primary resistive element is connected with the counter electrode.

\* \* \* \* \*